US011134880B2

(12) United States Patent
Rapin et al.

(10) Patent No.: US 11,134,880 B2
(45) Date of Patent: Oct. 5, 2021

(54) AUTOMATIC METHOD TO DELINEATE OR CATEGORIZE AN ELECTROCARDIOGRAM

(71) Applicant: Cardiologs Technologies SAS, Paris (FR)

(72) Inventors: Jeremy Rapin, Paris (FR); Jia Li, Paris (FR); Mathurin Massias, Paris (FR)

(73) Assignee: Cardiologs Technologies SAS, Paris (FR)

( * ) Notice: Subject to any disclaimer, the term of this patent is extended or adjusted under 35 U.S.C. 154(b) by 0 days.

(21) Appl. No.: 17/023,977

(22) Filed: Sep. 17, 2020

(65) Prior Publication Data

US 2021/0000365 A1    Jan. 7, 2021

Related U.S. Application Data

(63) Continuation of application No. 15/771,807, filed as application No. PCT/EP2016/075972 on Oct. 27, (Continued)

(30) Foreign Application Priority Data

Oct. 27, 2015   (EP) .................................... 15191769
Mar. 30, 2018   (EP) .................................... 18305376

(51) Int. Cl.
*A61B 5/046* (2006.01)
*A61B 5/0472* (2006.01)
(Continued)

(52) U.S. Cl.
CPC .............. *A61B 5/361* (2021.01); *A61B 5/316* (2021.01); *A61B 5/349* (2021.01); *A61B 5/364* (2021.01);
(Continued)

(58) Field of Classification Search
CPC ... A61B 5/046; A61B 5/04012; A61B 5/0452; A61B 5/0472; A61B 5/7264;
(Continued)

(56) References Cited

U.S. PATENT DOCUMENTS 5,024,225 A   6/1991   Fang
5,239,494 A   8/1993   Golbeck
(Continued)

FOREIGN PATENT DOCUMENTS

CA    2466848 A1    6/2003
CN    101268938 A   9/2008
(Continued)

OTHER PUBLICATIONS

Martinez et al "A wavelet-based ECG delineator", IEEE transactions on biomedical engineering, vol. 51, No. 4, Apr. 2004, 570-581. (Year: 2004).*

(Continued)

*Primary Examiner* — Erin M Piateski
(74) *Attorney, Agent, or Firm* — Eversheds Sutherland (US) LLP; Christopher C. Bolten; Robert D. Ward

(57) ABSTRACT

Disclosed is a method for computerizing delineation and/or multi-label classification of an ECG signal, including: applying a neural network to the ECG, labelling the ECG, and optionally displaying the labels according to time with the ECG signal.

30 Claims, 9 Drawing Sheets

Related U.S. Application Data 2016, now Pat. No. 10,779,744, which is a continuation-in-part of application No. 14/924,239, filed on Oct. 27, 2015, now Pat. No. 10,426,364, application No. 17/023,977, filed on Sep. 17, 2020, which is a continuation-in-part of application No. 16/367,227, filed on Mar. 27, 2019, now Pat. No. 10,827,938.

(51) Int. Cl.

| | |
|---|---|
| *A61B 5/00* | (2006.01) |
| *G16H 50/30* | (2018.01) |
| *A61B 5/0452* | (2006.01) |
| *A61B 5/04* | (2006.01) |
| *G16H 50/20* | (2018.01) |
| *A61B 5/361* | (2021.01) |
| *A61B 5/349* | (2021.01) |
| *A61B 5/366* | (2021.01) |
| *A61B 5/316* | (2021.01) |
| *A61B 5/364* | (2021.01) |

(52) U.S. Cl.
CPC .......... *A61B 5/366* (2021.01); *A61B 5/7264* (2013.01); *G16H 50/20* (2018.01); *G16H 50/30* (2018.01); *A61B 5/7203* (2013.01); *A61B 5/7221* (2013.01); *A61B 5/7267* (2013.01); *A61B 5/7282* (2013.01)

(58) Field of Classification Search
CPC ... A61B 5/7203; A61B 5/7221; A61B 5/7267; A61B 5/7282; G16H 50/30; G16H 50/20
USPC ....................................................... 600/518
See application file for complete search history.

(56) References Cited

U.S. PATENT DOCUMENTS

| | | |
|---|---|---|
| 5,619,991 A | 4/1997 | Sloane |
| 5,623,935 A | 4/1997 | Faisandier |
| 5,819,007 A | 10/1998 | Elghazzawi |
| 5,907,291 A | 5/1999 | Chen et al. |
| 5,966,692 A | 10/1999 | Langer et al. |
| 6,024,699 A | 2/2000 | Surwit et al. |
| 6,157,850 A | 12/2000 | Diab et al. |
| 6,507,753 B1 | 1/2003 | Xue et al. |
| 6,612,985 B2 | 9/2003 | Eiffert et al. |
| 6,656,125 B2 | 12/2003 | Misczynski et al. |
| 6,694,177 B2 | 2/2004 | Eggers et al. |
| 7,142,907 B2 | 11/2006 | Xue et al. |
| 7,289,844 B2 | 10/2007 | Misczynski et al. |
| 7,941,207 B2 | 5/2011 | Korzinov |
| 8,332,017 B2 | 12/2012 | Tarassenko et al. |
| 8,668,644 B2 | 3/2014 | Ong et al. |
| 8,818,496 B2 | 8/2014 | Dziubinski et al. |
| D717,955 S | 11/2014 | Bishay et al. |
| 8,903,479 B2 | 12/2014 | Zoicas |
| 8,932,220 B2 | 1/2015 | Ong et al. |
| 8,951,193 B2 | 2/2015 | Ong et al. |
| D744,659 S | 12/2015 | Bishay et al. |
| 9,241,650 B2 | 1/2016 | Amirim |
| 9,254,095 B2 | 2/2016 | Galloway et al. |
| 9,295,429 B2 | 3/2016 | Ong et al. |
| 9,339,202 B2 | 5/2016 | Brockway et al. |
| 9,345,414 B1 | 5/2016 | Bardy et al. |
| 9,351,652 B2 | 5/2016 | Dziubinski et al. |
| 9,364,155 B2 | 6/2016 | Bardy et al. |
| 9,408,545 B2 | 8/2016 | Felix et al. |
| 9,408,551 B2 | 8/2016 | Bardy et al. |
| 9,420,957 B2 | 8/2016 | Ong et al. |
| D766,447 S | 9/2016 | Bishay et al. |
| 9,433,367 B2 | 9/2016 | Felix et al. |
| 9,433,380 B1 | 9/2016 | Bishay et al. |
| 9,468,386 B2 | 10/2016 | Braojos Lopez et al. |
| 9,504,423 B1 | 11/2016 | Bardy et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,615,763 B2 | 4/2017 | Felix et al. |
| 9,619,660 B1 | 4/2017 | Felix et al. |
| 9,642,537 B2 | 5/2017 | Felix et al. |
| 9,655,537 B2 | 5/2017 | Bardy et al. |
| 9,655,538 B2 | 5/2017 | Felix et al. |
| 9,700,227 B2 | 7/2017 | Bishay et al. |
| D793,566 S | 8/2017 | Bishay et al. |
| 9,717,432 B2 | 8/2017 | Felix et al. |
| 9,717,433 B2 | 8/2017 | Felix et al. |
| 9,730,593 B2 | 8/2017 | Felix et al. |
| 9,730,641 B2 | 8/2017 | Felix et al. |
| 9,737,211 B2 | 8/2017 | Bardy et al. |
| 9,737,224 B2 | 8/2017 | Bardy et al. |
| D801,528 S | 10/2017 | Bardy et al. |
| 9,775,536 B2 | 10/2017 | Felix et al. |
| 9,788,722 B2 | 10/2017 | Bardy et al. |
| 9,820,665 B2 | 11/2017 | Felix et al. |
| 9,901,274 B2 | 2/2018 | Bishay et al. |
| 9,936,875 B2 | 4/2018 | Bardy et al. |
| 9,955,885 B2 | 5/2018 | Felix et al. |
| 9,955,888 B2 | 5/2018 | Felix et al. |
| 9,955,911 B2 | 5/2018 | Bardy et al. |
| 10,004,415 B2 | 6/2018 | Bishay et al. |
| 10,045,709 B2 | 8/2018 | Bardy et al. |
| 10,052,022 B2 | 8/2018 | Bardy et al. |
| D831,833 S | 10/2018 | Bishay et al. |
| 10,111,601 B2 | 10/2018 | Bishay et al. |
| 10,123,703 B2 | 11/2018 | Bardy et al. |
| 10,154,793 B2 | 12/2018 | Felix et al. |
| D838,370 S | 1/2019 | Bardy et al. |
| 10,165,946 B2 | 1/2019 | Bardy et al. |
| 10,172,534 B2 | 1/2019 | Felix et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,426,364 B2 | 10/2019 | Rapin et al. |
| 2001/0029338 A1 | 10/2001 | Krishnamachari |
| 2003/0176795 A1* | 9/2003 | Harris ............... A61B 5/7264 600/485 |
| 2004/0147840 A1* | 7/2004 | Duggirala ........... G06T 7/0012 600/437 |
| 2004/0230105 A1 | 11/2004 | Geva et al. |
| 2004/0260192 A1 | 12/2004 | Yamamoto |
| 2005/0101873 A1 | 5/2005 | Misczynski et al. |
| 2005/0113706 A1 | 5/2005 | Prystowsky et al. |
| 2005/0171448 A1 | 8/2005 | Korzinov et al. |
| 2005/0182334 A1 | 8/2005 | Korzinov et al. |
| 2005/0222508 A1* | 10/2005 | Moreno ............ A61B 5/04525 600/509 |
| 2008/0103403 A1 | 5/2008 | Cohen |
| 2008/0132799 A1 | 6/2008 | Xue |
| 2009/0112110 A1 | 4/2009 | Zhang |
| 2009/0192394 A1* | 7/2009 | Guttag ............... A61B 5/0452 600/509 |
| 2010/0268103 A1 | 10/2010 | McNamara et al. |
| 2011/0224565 A1 | 9/2011 | Ong et al. |
| 2011/0257548 A1 | 10/2011 | Dong et al. |
| 2012/0110226 A1 | 5/2012 | Vlach et al. |
| 2012/0278099 A1 | 11/2012 | Kelly et al. |
| 2013/0116585 A1 | 5/2013 | Bouguerra |
| 2013/0237776 A1 | 9/2013 | Ong et al. |
| 2014/0005988 A1 | 1/2014 | Brockway |
| 2014/0148714 A1 | 5/2014 | Mamaghanian et al. |
| 2014/0187988 A1 | 7/2014 | Ong et al. |
| 2015/0008802 A1 | 1/2015 | Fukuda |
| 2015/0088020 A1 | 3/2015 | Dreisbach et al. |
| 2015/0088024 A1 | 3/2015 | Sackellares et al. |
| 2015/0164349 A1 | 6/2015 | Gopalakrishnan et al. |
| 2015/0190067 A1 | 7/2015 | Prystowsky et al. |
| 2015/0248534 A1 | 9/2015 | Krzywicki et al. |

(56) References Cited

U.S. PATENT DOCUMENTS

| | | | |
|---|---|---|---|
| 2015/0257668 A1* | 9/2015 | Braojos Lopez | A61B 5/7267 600/512 |
| 2015/0282726 A1 | 10/2015 | Grube et al. | |
| 2017/0112401 A1 | 4/2017 | Rapin et al. | |
| 2017/0238833 A1 | 8/2017 | Felix et al. | |
| 2017/0251948 A1 | 9/2017 | Felix et al. | |
| 2017/0258358 A1 | 9/2017 | Bishay et al. | |
| 2017/0340290 A1 | 11/2017 | Felix et al. | |
| 2017/0357764 A1 | 12/2017 | Fauss et al. | |
| 2017/0367609 A1 | 12/2017 | Bardy et al. | |
| 2018/0028144 A1 | 2/2018 | Chen et al. | |
| 2018/0177423 A1 | 6/2018 | Bishay et al. | |
| 2018/0279956 A1 | 10/2018 | Waydo et al. | |
| 2018/0296118 A1 | 10/2018 | Bishay et al. | |
| 2018/0310892 A1 | 11/2018 | Perschbacher et al. | |
| 2018/0344191 A1 | 12/2018 | Bardy et al. | |
| 2018/0353071 A1 | 12/2018 | Bardy et al. | |
| 2019/0059763 A1 | 2/2019 | Shakur et al. | |
| 2019/0069794 A1 | 3/2019 | Bardy et al. | |
| 2019/0069798 A1 | 3/2019 | Bardy | |
| 2019/0069800 A1 | 3/2019 | Bardy et al. | |
| 2019/0076023 A1 | 3/2019 | Bardy et al. | |
| 2019/0090769 A1 | 3/2019 | Boleyn et al. | |
| 2019/0099105 A1 | 4/2019 | Felix et al. | |
| 2019/0104961 A1 | 4/2019 | Felix et al. | |
| 2019/0117099 A1 | 4/2019 | Bardy et al. | |
| 2019/0117107 A1 | 4/2019 | Felix et al. | |
| 2019/0133444 A1 | 5/2019 | Bardy et al. | |
| 2019/0133486 A1 | 5/2019 | Felix et al. | |
| 2019/0167143 A1 | 6/2019 | Li et al. | |
| 2019/0223739 A1 | 7/2019 | Rapin et al. | |
| 2019/0298204 A1 | 10/2019 | Fontanarava et al. | |
| 2020/0015694 A1 | 1/2020 | Rapin et al. | |
| 2020/0022604 A1 | 1/2020 | Scabellone et al. | |

FOREIGN PATENT DOCUMENTS

| | | | |
|---|---|---|---|
| CN | 101766484 | A | 7/2010 |
| CN | 102188240 | A | 9/2011 |
| CN | 102379694 | A | 3/2012 |
| CN | 102779234 | A | 11/2012 |
| CN | 103038772 | A | 4/2013 |
| CN | 103110417 | A | 5/2013 |
| CN | 103284702 | A | 9/2013 |
| CN | 103417209 | A | 12/2013 |
| CN | 104463326 | A | 3/2015 |
| CN | 104970789 | A | 10/2015 |
| CN | 106778685 | A | 5/2017 |
| DE | 60127354 | T2 | 12/2007 |
| EP | 0465241 | A2 | 1/1992 |
| EP | 0465241 | B1 | 11/1998 |
| EP | 1179319 | A1 | 2/2002 |
| EP | 1503664 | A2 | 2/2005 |
| EP | 2030565 | A1 | 3/2009 |
| EP | 2534597 | A2 | 12/2012 |
| EP | 3144851 | A1 | 3/2017 |
| EP | 2534597 | B1 | 10/2018 |
| JP | 2002172096 | A | 6/2002 |
| JP | 2013524865 | A | 6/2013 |
| KR | 20150020955 | A | 2/2015 |
| WO | WO-03045224 | A2 | 6/2003 |
| WO | WO-03045224 | A3 | 11/2004 |
| WO | WO-2006048881 | A2 | 5/2006 |
| WO | WO-2011115576 | A2 | 9/2011 |
| WO | WO-2016145392 | A1 | 9/2016 |
| WO | WO-2017072250 | A1 | 5/2017 |
| WO | WO-2019038435 | A1 | 2/2019 |
| WO | WO-2019089830 | A1 | 5/2019 |

OTHER PUBLICATIONS

Alfonso, et al., ECG Beat Detection Using Filter Banks, Transactions on Biomedical Engineering, ) Saint Paul, MN USA, 46(2): 192-202 (Feb. 1999).

Almeida, et al., Multilead ECG Delineation Using Spatially Projected Leads From Wavelet Transform Loops, IEEE transactions on biomedical engineering, Zaragoza, Spain, 56(8): 1996-2005 (Aug. 2009).

Badilini, et al., ECGScan: A Method for Conversion of Paper Electrocardiographic Printouts to Digital Electrocardiographic Files, Journal of Electrocardiology, 38:310-318 (2005).

Bishop, Pattern Recognition and Machine Learning, Springer, Information Science and Statistics, 2006, ISBN-10: 0-387-31073-8, New York, NY, USA.

Boichat, et al., Wavelet-Based ECG Delineation on a Wearable Embedded Sensor Platform, Proceedings of Wearable and Implantable Body Sensor Networks, 2009, Madrid, Spain (pp. 256-261).

Casimir C. "Casey" Klimasauskas; "Neural Nets and Noise Filtering", Dr. Dobb's Journal, pp. 32—Jan. 1989, Sewickley, PA.

Chazal, et al., A Patient-Adapting Heartbeat Classifier Using ECG Morphology and Heartbeat Interval Features, IEEE Transactions on Biomedical Engineering, Dublin, Ireland, 53(12):2535-2543 (Dec. 2006).

Chazal, et al., Automatic Classification of Heartbeats Using ECG Morphology and Heartbeat Interval Features, IEEE Transactions on Biomedical Engineering, Dublin, Ireland, 51(7):1196-1206 (Jul. 2004).

Chebil, et al., A Novel Method for Digitizing Standard ECG Papers, Proceedings of the International Conference on Computer and Communication Engineering 2008, May 13-15, 2008, Kuala Lumpur, Malaysia (pp. 1308-1312).

Choi, et al., Development of ECG Beat Segmentation Method by Combining Lowpass Filter and Irregular R-R Interval Checkup Strategy, Expert Systems with Applications, Seoul, Republic of Korea, 37:5208-5218 (2010).

Coast, et al., An Approach to Cardiac Arrhythmia Analysis Using Hidden Markov Models, IEEE transactions on biomedical engineering, Pittsburgh, PA, US, 37(9):826-836 (Sep. 1990).

Cybenko, Approximation by Superpositions of a Sigmoidal Function, Mathematics of Control, Signals and Systems, Urbana, Illinois, USA, 2:303-314 (1989).

Donahue et al., Long-term Recurrent Convolutional Networks for Visual Recognition and Description, arXiv:1411.4389v3, Feb. 17, 2015, Berkeley, CA, USA, (pp. 1-13).

Dubois, et al., Automatic ECG Wave Extraction in Long-Term Recordings using Gaussian Mesa Function Models and Nonlinear Probability Estimators, Computer Methods and Programs in Biomedicine, Paris, France, 88:217-233 (Mar. 2007).

European Search Report & Written Opinion dated Oct. 15, 2018 in EP Patent Appl. Serial No. 18305376.8 (0530).

European Search Report dated Apr. 13, 2016 in EP Patent Appl. Serial No. 15191769.7 (0230).

Francois, Portet., P Wave Detector with PP Rhythm Tracking: Evaluation in Different Arrhythmia Contexts, Physiological Measurement, Institute of Physics: Hybrid Open Access, Scotland, UK, 2008, (pp. 141-155).

Fukushima, Neocognitron: A Self-organizing Neural Network Model for a Mechanism of Pattern Recognition Unaffected by Shift in Position, Biological Cybernetics, Tokyo, Japan, 36:193-202 (1980).

Hughes, et al., Markov Models for Automated ECG Interval Analysis, Proceedings of Neural Information Processing Systems, 2004, Oxford, UK, (pp. 611-618).

Ieva, et al., Multivariate Functional Clustering for the Morphological Analysis of Electrocardiograph Curves, Journal of the Royal Statistical Society: Series C (Applied Statistics), Blackwell Publishing Ltd, London, UK, 62:401-418 (2013).

International Search Report & Written Opinion dated Aug. 1, 2019 in Int'l PCT Patent Appl. No. PCT/IB2019/052517 (0510).

International Search Report & Written Opinion dated Nov. 21, 2018 in Int'l PCT Patent Appl. Serial No. PCT/EP2018/072912 (0410).

International Search Report & Written Opinion dated Jun. 4, 2020 in PCT Patent Appl. Serial No. PCT/IB2020/050850 (0710 PCT).

International Search Report & Written Opinion dated Jan. 24, 2017 in Int'l PCT Patent Appl. Serial No. PCT/EP2016/075972 (0310).

Jin, et al., Deep Learning Research on Clinical Electrocardiogram Analysis, Science China Press, 45(3):398-416 (2015), China, English abstract provided.

(56) References Cited

OTHER PUBLICATIONS

Johnson, et al., R-Peak Estimation using Multimodal Lead Switching, Computing in Cardiology 2014, pp. 281-284, Oxford, UK.

Kaur et al., Comparison of Different Approaches for Removal of Baseline Wander From ECG Signal, Proceedings published by International Journal of Computer Applications, 2011, Sangrur (Pb.), India, (pp. 30-36).

Kiranyaz, et al., Convolutional Neural Networks for Patient-Specific ECG Classification, 37th annual international conference of the IEEE engineering in medicine and biology society, Aug. 2015, Doha, Qatar, (pp. 2608-2611).

Kiranyaz, et al., Real-Time Patient-Specific ECG Classification by 1-D Convolutional Neural Networks, IEEE transactions on Biomedical Engineering, Doha, Qatar, 63(3):664-675 (Mar. 2015).

Krizhevsk, et al., ImageNet Classification with Deep Convolutional Neural Networks, Proceedings of Neural Information Processing Systems, Toronto, Canada, 2012, (pp. 1097-1105).

Laguna, et al., A Database for Evaluation of Algorithms for Measurement of QT and Other Waveform Intervals in the ECG, Computers in Cardiology, Spain, 24:673-676 (1997).

Lecun, et al., Backpropagation Applied to Handwritten Zip Code Recognition, Neural Computation, Holmdel, NJ, USA, 1:541-551 (1989).

Li, et al., Deep neural networks Improve Atrial Fibrillation Detection in Holter: first results, European Journal of Preventive Cardiology, European Congress on eCardiology & eHealth, Oct. 2016, Abstract, 23 (2S), 41 (2016).

Li, et al., Detection of ECG Characteristic Points Using Wavelet Transforms, Transactions on Biomedical Engineering, Shaanxi, P. R. China, 42(1):21-28 (1995).

Lin et al., Beat-to-beat P and T Wave Delineation in ECG Signals Using a Marginalized Particle Filter, Proceedings of EUSIPCO, 2012, Toulouse, France, (pp. 479-483).

Lin, et al., P and T Wave Delineation and Waveform Estimation in ECG Signals Using a Block Gibbs Sampler, Signal Processing Conference (EUSIPCO), Toulouse, France, 2012 (pp. 479-483).

Lin et al., P- and T-Wave Delineation in ECG Signals Using a Bayesian Approach and a Partially Collapsed Gibbs Sampler, IEEE Transactions on Biomedical Engineering, Toulouse, France, 57:2840-2849 (Dec. 2010).

Long, et al., Fully Convolutional Networks for Semantic Segmentation, Proceedings of Computer Vision and Pattern Recognition, Berkeley, CA, USA, 2015 (pp. 3431-3440).

Martinez et al., A Wavelet-Based ECG Delineator: Evaluation on Standard Databases, IEEE Transactions on Biomedical Engineering, Zaragoza, Spain, 51(4): 570-581 (Apr. 2004).

Matan, et al., Multi-Digit Recognition Using a Space Displacement Neural Network, Neural Information Processing Systems, Morgan Kaufmann, Holmdel, NJ USA, 1992 (pp. 488-495).

Meghriche, et al., On the Analysis of a Compound Neural Network for Detecting Atrio Ventricular Heart Block (AVB) in an ECG Signal, International Journal of Biological and Life Sciences, 4(1):1-11 (2008).

Megriche, et al., On the Analysis of a Compound Neural Network for Detecting Atrio Ventricular Heart Block (AVB) in a ECG Signal, World Academy of Science, Engineering and Technology, International Journal of Health and Medical Engineering, 2(3):68-78 (2008).

Mnih, et al., Recurrent Models of Visual Attention, Google DeepMind, arXiv:1406.6247v1, Jun. 24, 2014 (pp. 1-12).

Noda, et al., Audio-Visual Speech Recognition using Deep Learning, Appl. Intell. 2015, Springer Science, New York, NY USA, 40:722-737, (Dec. 20, 2014).

Nowlan, et al., A Convolutional Neural Network Hand Tracker, Advances in Neural Information Processing Systems 7, Morgan Kaufmann, Synaptics, Inc. San Jose, CA USA, 1995, (pp. 901-908).

Pan, et al., A Real-Time QRS Detection Algorithm, IEEE Transactions on Biomedical Engineering, Shanghai, P. R. of China, BME-32(3): 230-236, (Mar. 1985).

Pigoli, et al., Wavelets in Functional Data Analysis: Estimation of Multidimensional Curves and their Derivatives, Computational Statistics and Data Analysis, Politecnico di Milano, Italy, 56:1482-1498 (2012).

Prineas et al., The Minnesota Code Manual of Electrocardiographic Findings, Springer, Second Edition, ISBN 978-1-84882-777-6, 2009, Minneapolis, Minnesota, US.

Ravichandran, et al., Novel Tool for Complete Digitization of Paper Electrocardiography Data, IEEE Journal of Translational Engineering in Health and Medicine, Medical Imaging and Diagnostic Radiology, 1:7, (Jun. 2013).

Rodrigues, et al., A Neural Network Approach to ECG Denoising, CoRR, Caparica, Portugal, Dec. 2012, abs/1212.5217, (pp. 1-15).

Rosenblatt., The Perceptron: A Probabilistic Model for Information Storage and Organization in the Brain, Psychological Review, Buffalo, NY, USA, 65(6):386-408 (1958).

Russakovsky, et al., "ImageNet Large Scale Visual Recognition Challenge", arXiv:1409.0575v3, Stanford, CA, USA, Jan. 30, 2015 (pp. 1-43).

Saini, et al., Automated ECG Delineation using Machine Learning Algorithms, International Congress on Electrocardiology, Jalandhar, India, 2014, (pp. 1-4).

Schluter, et al., Improved Musical Onset Detection With Convolutional Neural Networks, IEEE International Conference on Acoustics, Speech, and Signal Processing ICASSP 2014, Linz, Austria, 99:1-5, (2014).

Shen, et al., Multi-Lead ECG Classification Based on Independent Component Analysis and Support Vector Machine, Biomedical Engineering and Informatics (BMEI), 3:960-964 (2010).

Simonyan, et al., Very Deep Convolutional Networks for Large-Scale Image Recognition, Published as a conference paper at ICLR, Apr. 10, 2015.

Smith, et al., Improved Interpretation of Atrial Dysrhythmias by a New Neural Network Electrocardiogram Interpretation Algorithm, Society for Academic Emergency Medicine Abstracts, 24 (S1), S235 (2017).

Statement of Validation and Accuracy for the Glasgow 12-Lead ECG Analysis Program, Physio Control, Mar. 2009, Redmond, WA USA.

Tun, et al., Analysis on conversion process from paper record ECG to computer based ECG,MOJ Applied Bionics and Biomechanics, 1(2):69-81 (2017).

Vaessen., An approach to ECG Delineation using Wavelet Analysis and Hidden Markov Models, Universiteit Maastricht Institute of Instrument Development Engineering & Evaluation Master Thesis, Sep. 2006.

Zeiler, Matthew D., Adadelta: An Adaptive Learning Rate Method, dated Dec. 22, 2012, prepared while at Google Inc., USA. (arXiv: 1212.5701 [cs.LG].

Zhang et al., Improving Object Detection with Deep Convolutional Networks via Bayesian Optimization and Structured Prediction, Computer Vision Foundation CVPR2015, pp. 249-258, Zhejiang, China.

Zheng, et al., Time Series Classification Using Multi-Channels Deep Convolutional Neural Networks, Web-Age Information Management, Switzerland, 8485:298-310, (2014).

\* cited by examiner

Second-degree AV block, Mobitz type I (Wenckebach) (100%)
IVCD-Intraventricular conduction delay (>110 ms) (100%)

AUTOMATIC METHOD TO DELINEATE OR CATEGORIZE AN ELECTROCARDIOGRAM

CROSS-REFERENCE TO RELATED APPLICATIONS

This application is a continuation of U.S. patent application Ser. No. 15/771,807, filed Apr. 27, 2018, now U.S. Pat. No. 10,779,744, which is a national phase application under 35 U.S.C. § 371 of PCT/EP2016/075972, filed Oct. 27, 2016, which is a continuation-in-part of U.S. patent application Ser. No. 14/924,239, filed Oct. 27, 2015, now U.S. Pat. No. 10,426,364, and claims priority to European Patent Application Serial No. 15191769.7, filed Oct. 27, 2015, the entire contents of each of which are incorporated herein by reference.

This application is also a continuation-in-part of U.S. patent application Ser. No. 16/367,227, filed Mar. 27, 2019, which claims priority to European Patent Application Serial No. 18305376.8, filed Mar. 30, 2018, the entire contents of each of which are incorporated herein by reference.

This application is related to U.S. patent application Ser. No. 16/622,648, filed Jul. 26, 2019, now U.S. Pat. No. 10,758,139, which is a divisional of U.S. patent application Ser. No. 14/924,239, filed Oct. 27, 2015, now U.S. Pat. No. 10,426,364, the entire contents of each of which are incorporated herein by reference.

This application is related to U.S. patent application Ser. No. 16/267,380, filed Feb. 4, 2019, which is a continuation-in-part of U.S. patent application Ser. No. 15/771,807, filed Apr. 27, 2018, now U.S. Pat. No. 10,779,744, which is a national phase application under 35 U.S.C. § 371 of PCT/EP2016/075972, filed Oct. 27, 2016, which is a continuation-in-part of U.S. patent application Ser. No. 14/924,239, filed Oct. 27, 2015, now U.S. Pat. No. 10,426,364, and claims priority to European Patent Application Serial No. 15191769.7, filed Oct. 27, 2015, the entire contents of each of which are incorporated herein by reference. U.S. patent application Ser. No. 16/267,380, filed Feb. 4, 2019, is also a continuation-in-part of PCT/EP2018/072912, filed Aug. 24, 2018, which claims priority to U.S. Provisional Patent Application Ser. No. 62/549,994, filed Aug. 25, 2017, the entire contents of each of which are incorporated herein by reference.

FIELD OF INVENTION

The present invention relates to temporal signal analysis, preferably cardiac signal analysis, more preferably electrocardiogram analysis, using at least one neural network.

BACKGROUND OF INVENTION

Electrocardiogram (ECG) and endocardiogram are graphic representations of the electrical activity of the heart. Electrocardiogram is recorded from the body using a number of electrodes placed in specific predefined areas. It is considered as a fundamental tool of clinical practice. It is a simple, non-invasive exam that can be performed by any health professional. Placing the electrodes is not considered as a medical procedure, yet in some countries, the prescription of the ECG by a doctor is essential for it to be performed. It is known that the ECG constitutes the first step in cardiovascular diseases (CVD) diagnosis, and is used multiple times throughout the life of a CVD patient. CVD constitute the first global cause of death.

A cardiac signal is composed of one or multiple synchronized temporal signals, called lead signals. The ECG shown in FIG. 1 represents a standard 12-lead resting ECG, with its 12 standard deviations recording during 10 seconds. Some ECG, specifically known as Holters, may record only one lead for a period of time which can be of more than 7 days.

A cardiac signal displays repeating patterns usually comprising a P-wave, a QRS complex and a T-wave, respectively corresponding to the depolarization of the atria, depolarization of the ventricles and repolarization of the ventricles. These waves and complexes are shown in FIG. 2, which focuses on a couple of beats in one lead signal.

Cardiac signals allow for the detection of many abnormalities, which often in turn point to specific CVD. It is estimated that about 150 measurable abnormalities can be identified on an ECG recordings today. However, without specific expertise and/or regular training, only a small portion of these abnormalities can be easily spotted. Unfortunately, today, it is estimated that only one third of ECGs are performed in settings where cardiology expertise is readily available.

In order to make cardiac signal interpretation, especially ECG interpretation simpler and assist non-specialists, two alternatives exist today, but neither fully satisfy the needs of health professionals:

Telecardiology centers, where an interpretation of an ECG sent by a non-specialist is delivered either by a cardiologist or by a specialized ECG technician. Their interpretations are of high quality but are slow and expensive to obtain.

Prior art automated cardiac signal interpretation softwares, which are mainly developed by cardiac signal device manufacturers. They provide low quality interpretation (false alarms are very frequent) but deliver them in seconds.

Prior art automated cardiac signal interpretation softwares can provide two types of information about a cardiac signal:

a local information called delineation, providing the temporal location of each wave and optionally qualifying each wave separately; and/or a global information providing a classification of the cardiac signal as normal/abnormal or labeling its abnormalities.

Concerning delineation, two main approaches are used for finding the waves of cardiac signals.

The first one is based on multiscale wavelet analysis. This approach looks for wavelet coefficients reaching predefined thresholds at well-chosen scales (Martinez et al, IEEE transactions on biomedical engineering, Vol. 51, No. 4, April 2004, 570-581, Almeida et al., IEEE transactions on biomedical engineering, Vol. 56, No. 8, August 2009, pp 1996-2005, Boichat et al., Proceedings of Wearable and Implantable Body Sensor Networks, 2009, pp 256-261, U.S. Pat. No. 8,903,479, Dec. 2, 2014, Zoicas et al.). The usual process is to look for QRS complexes, and then look for P waves on the signal before the complexes, and after them for T waves. This approach can only handle a single lead at a time, sometimes using projection to one artificial lead (US 2014/0148714—May 29, 2014, Mamaghanian et al.). This computation is made very unstable by the use of thresholds. The approach is also limited as it can neither deal with multiple P waves nor with "hidden" P waves.

The second one is based on Hidden Markov Models (HMM). This machine learning approach considers that the current state of the signal (whether a sample is either part of a QRS complex, a P wave, a T wave or no wave) is a hidden variable that one wants to recover (Coast et al., IEEE transactions on biomedical engineering, Vol. 37, No. 9, September 1990, pp 826-836, Hughes et al., Proceedings of Neural Information Processing Systems, 2004, pp 611-618, U.S. Pat. No. 8,332,017, Dec. 11, 2012, Trassenko et al.). To this end, a representation of the signal must be designed using handcrafted "features", and a mathematical model must be fitted for each wave, based on these features. Based on a sufficient number of examples, the algorithms can learn to recognize each wave. This process can however be cumbersome since the feature design is not straightforward, and the model, usually Gaussian, is not well adapted. Also, none of these works has considered the situation of hidden P waves.

In the state-of-the-art, characterization of the waves for the delineation is only performed on the QRS to detect for instance ventricular or paced heats, and done in a second step, once the waves have already been localized. Such methods usually use standard classification algorithms which learn the type of beat based on many training examples of handcrafted set of features and corresponding beat label (Ghazal et al., *IEEE Transactions on Biomedical Engineering,* 2004, vol. 51, pp. 1196-1206). These methods are limited in that the features which have been handcrafted will always be suboptimal since they were not learnt and may have erased some crucial information.

In order to solve the above issues, the latest works (Kiranyaz et al, *IEEE Transactions on Biomedical Engineering,* 2016, Vol. 63, pp 664-675) have turned to novel architectures called neural networks which have been intensively studied and had great results in the field of imaging (Russakovsky et al., arXiv:1409.0575v3, 30 Jan. 2015). Indeed, these methods bypass the need of handcrafted features and directly learn from raw or mildly preprocessed data. Still, these applications of neural networks to cardiac signal waves characterization are very limited since;

they must first rely on an algorithm able to detect the waves;

they were only developed for QRS characterization; and they lack context information in processing one beat at a time, surrounding beats often providing important information.

Concerning abnormalities and/or CVD detection, most algorithms use rules based on temporal and morphological indicators computed using the delineation: PR, RR and QT intervals, QRS width, level of the ST segment, slope of the T wave, etc . . . . These rules such as the Minnesota Code (Prineas et al., Springer, ISBN 978-1-84882-777-6, 2009) were written by cardiologists. However, they do not reflect the way the cardiologists analyze the ECGs and are crude simplifications. Algorithms such as the Glasgow University Algorithm are based on such principles (Statement of Validation and Accuracy for the Glasgow 12-Lead ECG Analysis Program, Physio Control, 2009).

More advanced methods use learning algorithms, and are built using a diagnosis and an adequate representation for each cardiac signal they learn from. In, Shen et al., *Biomedical Engineering and Informatics (BMEI).* 2010, vol. 3, pp. 960-964 for instance, the author used support vector machines to detect bundle branch blocks. However, in these methods, once again, it is necessary to seek a representation of the raw data into a space that preserves the invariance and stability properties. Indeed, cardiac signals vary significantly from one patient to another. It is therefore extremely difficult for an algorithm to learn how to discriminate different diseases by simply comparing raw data. A representation which drastically limits this interpatient variability while preserving the invariance within the same disease class must be chosen. Also, once again these representations usually rely on a preliminary detection of the beats and hence in a reliable delineation.

Some scientific teams very recently also turned to neural network architectures, but limitations still arose when they attempted to apply them to ECGs.

One team (Jin and Dong, Science China Press, Vol. 45, No 3, 2015, pp 398-416; CN104970789) proposed binary classification on a full ECG, hence providing one and only one class for any analyzed ECG. This is for instance a classification normal Vs abnormal (see [0027] of CN104970789). Their architecture use convolutional layers which process the leads independently before mixing them into fully connected layers. The authors also mention multi-class analysis, aiming at recovering one class among several, but they do not consider the less commonly used multi-label classification, which is however crucial in ECG analysis since one ECG can have several abnormalities such as for instance a left bundle branch block with atrial fibrillations.

Thus, there is a need for methods able to analyze cardiac signal, especially ECG, that can:

carry out the analysis without the need for beat-by-beat processing, or feature extraction;

obtain the delineation of the signal, including identification of hidden P waves, qualification of each wave in a single step, and optionally present this information in an comprehensible way;

provide a multi-label classification directly from at least one time window of a cardiac signal, generally exhibiting multiple labels, contrary the prior art, which provides a single exclusive label;

process data with varying number of leads with a same neural network;

be fast, stable and reliable.

SUMMARY

To address the above issues in cardiac signal analyses, the Applicant developed two techniques based on convolutional neural networks:

A convolutional neural network which first gives a dense prediction of the probability of presence of each wave on each time stamp of the cardiac signal, then post-processes the signal to produce its delineation. This novel approach of the delineation, using convolutional networks, allows the processing of cardiac signals of any duration, analyzing and qualifying all types of waves in the same way in a single step, without being constrained by their positions.

A convolutional neural network which directly predicts multiple labels on the cardiac signal. It results in a fixed format multi-label output which can represent abnormalities such as for instance "Atrial fibrillations" or descriptors such as for instance "Normal sinus rhythm" or "Noisy ECG".

Thus, the present invention relates to a method for computerizing the delineation of a cardiac signal comprising a plurality of time points, said method comprising: applying a convolutional neural network NN1 to said cardiac signal, whereby the convolutional neural network NN1 reads each time point of the cardiac signal, analyzes temporally each time point of the cardiac signal, assigns to each time point of the cardiac signal a score for at least one wave among the following waves: P-wave, QRS complex, T-wave.

According to one embodiment, the convolutional neural network NN1 assigns to each time point of the cardiac signal a score for at least the following waves: P-wave, QRS complex, T-wave. According to one embodiment, the convolutional neural network assigns to each time point of the cardiac signal a score for the hidden P waves, According to one embodiment, the convolutional neural network NN1 is a fully convolutional neural network.

According to an embodiment, the method further comprises a pre-treatment step, wherein the pre-treatment comprises denoising and removing the baseline of the cardiac signal as well as expressing it at a chosen frequency prior to the application of NN1.

According to an embodiment, the method further comprises a post-treatment step computing the time points of the beginning and the end of each wave in the cardiac signal, called the onset and the offset, and other information such as for instance prematurity, conduction and origin of the waves. According to one embodiment, the method further comprises a post-treatment step computing global or local measurements based on the onset and the offset of each wave and the signal, such as for instance PR interval, ST elevation and heart rate. According to one embodiment, the method further comprises a post-treatment step computing delineation-based labels based on the global or local measurements.

According to one embodiment, the convolutional neural network NN1 is able to process a cardiac signal recorded from any number of leads.

The invention also comprises a software comprising a trained neural network for delineation of a cardiac signal. The invention also comprises a computer device comprising a software implementing a method for delineation of a cardiac signal, comprising applying a convolutional neural network NN1 to said cardiac signal, as described above. According to one embodiment, the computer device further comprises a display configured for displaying the wave locations and optionally simultaneously the cardiac signal and/or an application programming interface for recovering the delineation-based labels and/or delineation for any given cardiac signal.

This invention also includes a method for computerizing multi-label classification of a cardiac signal having a plurality of time points, comprising applying a convolutional neural network NN2 to said cardiac signal, whereby the convolutional neural network NN2 reads each time point of the cardiac signal, analyzes each time point of the cardiac signal, computes scores on a time window aggregating at least two time points for a plurality of predetermined non-exclusive labels, such as for instance normal cardiac signal, artefact or atrial fibrillation, and allots to the time window the labels which have a score higher than at least one predetermined threshold.

According to one embodiment the convolutional neural network NN2 is a recurrent neural network.

According to an embodiment, the method further comprises a pre-treatment step, wherein the pre-treatment comprises denoising and removing the baseline of the cardiac signal as well as expressing it at a chosen frequency prior to the application of NN2.

According to an embodiment, the method further comprises a post-treatment step, comprising a filtering step so as to remove redundant labels, and optionally incorporating delineation-derived labels such as for instance first degree atrioventricular block (long PR interval), and optionally computing the onset and offset times of each abnormality. According to one embodiment, the convolutional neural network NN2 is able to process a cardiac signal recorded from any number of leads.

The invention also comprises a software comprising a trained neural network for multi-label classification of a cardiac signal. The invention also comprises a computer device comprising a software implementing a method for multi-label classification of a cardiac signal, comprising applying a recurrent neural network NN2 to said cardiac signal, as described above. According to one embodiment, the computer device further comprises a display configured for displaying the scores of the labels which have been allotted to a time window and optionally simultaneously the cardiac signal; and/or an application programming interface for recovering the labels.

Furthermore, the invention also concerns a method for computerizing multi-label classification of a cardiac signal, having a plurality of time points, said method comprising applying a convolutional neural network NN1 to said cardiac signal, wherein the neural network: reads each time point of the cardiac signal, analyzes temporally each time point of the cardiac signal, assigns to each time point of the cardiac signal a score for at least the following waves: P-wave, QRS complex, T-wave; computes the onset and the offset of each wave in the cardiac signal based on the scores assigned to each time point; computes global measurements based on the onset and the offset of each wave; and applying a convolutional neural network NN2 to said cardiac signal, wherein the neural network: reads each time point of the cardiac signal and the global measurements obtained from NN1, analyzes each time point of the cardiac signal and the global measurements obtained from NN, computes scores on a time window aggregating at least two time points far a plurality of predetermined non-exclusive labels, such as for example normal cardiac signal, artefact or, atrial fibrillation, allots to the time window the labels which have a score higher than the predetermined threshold.

According to one embodiment, the method further comprises a pre-treatment step, wherein the pre-treatment comprises denoising and removing the baseline of the cardiac signal as well as expressing it at a chosen frequency prior to the application of NN1 and NN2. According to one embodiment, the method further comprises a post-treatment step computing delineation-based labels, removing redundant labels, and optionally computing onset and offset of each abnormality. According to one embodiment, the convolutional neural networks are able to process a cardiac signal recorded from any number of leads. The invention also comprises a software comprising a trained neural network for delineation of a cardiac signal. The invention also comprises a computer device comprising a software implementing said method, comprising applying convolutional neural networks NN1 and NN2 to said cardiac signal, as described above. According to one embodiment, the computer device further comprises a display configured for displaying the wave locations, the scores of the labels which have, been allotted to a time window and optionally simultaneously the cardiac signal; and/or an application programming interface for recovering the labels and/or delineation for any given cardiac signal.

Furthermore, the invention also includes a method for computerizing delineation and multi-label classification of a cardiac signal having a plurality of time points, comprising applying a trained neural network NN3 to said cardiac signal, whereby the recurrent neural network NN3 reads each time point of the cardiac signal, analyzes temporally each time point of the cardiac signal, assigns to each time point of the cardiac signal a score for at least the following waves: P-wave, QRS complex, T-wave; computes scores on a time window aggregating at least two time points for a plurality of predetermined non-exclusive labels, such as for example normal cardiac signal, artefact or atrial fibrillation;

and allots to the time window the labels which have a score higher than at least one predetermined threshold.

According to an embodiment, the method further comprises a pre-treatment step, wherein the pre-treatment comprises denoising and removing the baseline of the cardiac signal as well as expressing it at a chosen frequency prior to the application of NN3.

According to one embodiment, the method further comprises a post-treatment step computing the onset and offset of each wave in the cardiac signal optionally with other information such as for instance prematurity, conduction and origin of the waves; computing delineation-derived labels; removing redundant labels, and optionally producing onset and offset of each abnormality and global and local measurements such as for instance PR interval and heart rate.

The invention also comprises a software comprising a trained neural network for delineation and multi-label classification of a cardiac signal. The invention also comprises a computer device comprising a software implementing a method for delineation and multi-label classification of a cardiac signal, comprising applying a neural network NN3 to said cardiac signal, as described above. According to one embodiment, the computer device further comprising a display configured for displaying the wave locations, the scores of the labels which have been allotted to a time window and optionally simultaneously the cardiac signal; and/or an application programming interface for recovering the labels and/or delineation for any given cardiac signal.

Definition

"Abnormality" refers to any physiological abnormality which can be identifiable on the cardiac signal. Today about 150 measurable abnormalities can be identified on cardiac signal recordings. For instance, within the present invention, the following abnormalities may be nonlimitatively identified: "Sinoatrial block, paralysis or arrest", "Atrial Fibrillation", "Atrial fibrillation or flutter", "Atrial Flutter", "Atrial tachycardia", "Junctional tachycardia", "Supraventricular tachycardia", "Sinus tachycardia", "Ventricular tachycardia", "Pacemaker", "Premature ventricular complex", "Premature atrial complex", "First degree atrio-ventricular block (AVE)", "$2^{nd}$ degree AVB Mobitz I", "$2^{nd}$ degree AVB Mobitz II", "$3^{rd}$ degree AVB", "Wolff-Parkinson-White syndrome", "Left bundle branch block", "Right bundle branch block", "Intraventricular conduction delay", "Left ventricular hypertrophy", "Right ventricular hypertrophy", "Acute myocardial infarction", "Old myocardial infarction", "Ischemia", "Hyperkalemia", "Hypokalemia", "Brugada", "Long QTc", etc . . . .

"Cardiac signal" refers to the signal recording the electrical conduction in the heart. Said cardiac signal may be for instance an electrocardiogram (ECG) or an endocardiogram. Such signals may have one or more channels, called leads. It may be short term (10 seconds in standard ECGs) or long term (several days in Hollers).

"Classification" refers to the task of categorizing objects into a list of groups. Such a task includes for instance recognizing the animal from a picture (the list of groups is then a list of animals), or recognizing whether an ECG is normal or abnormal.

"Multi-label classification" refers to identifying objects as being part of none, one or several groups of a given list of groups. Such a task includes for instance identifying none to several animals from a picture, or identifying none to several abnormalities on an ECG.

"Delineation" refers to the identification of the temporal localization of each of the waves of a cardiac signal. Delineation can also optionally provide more precise characterization of each of the waves.

"Descriptor" refers to a description of a cardiac signal which is not an abnormality, such as for instance "Normal ECG", "Normal sinus rhythm" or "Noisy cardiac signal", "Electrode inversion", etc . . . .

"Hidden P wave" refers to a P wave which occurs during another wave or complex, such as for example during a T wave.

"Label" refers to a class used within the present invention for multi-label classification of a cardiac signal. Said label can be an abnormality or a descriptor. Labels are none exclusive. For instance, one can observe an Atrial fibrillation and Wolff-Parkinson-White together.

"Delineation-based labels" refers to labels which can be deduced (i.e. computed) from the delineation and its measurements. For instance, within the present invention, the following delineation-based labels may be nonlimitatively: "short PR interval" (PR interval<1120 ms), "First degree AV block" (PR interval>200 ms), axis deviations, "Long QTc", "Short QTc", "Wide complex tachycardia", intraventricular conduction blocks, etc . . . .

"Local measurements" refers to measurements directly derived from the delineation, such as for instance a given RR interval (duration between one QRS complex and the following).

"Global measurements" refers to measurements derived from the delineation and aggregated through time, such as for instance a mean or median values of PR interval (duration between the beginning of a conducted P wave and the following QRS complex), P duration, QRS duration, QRS axis, median QT interval, corrected QT inverval (Qtc), corrected JT interval, heart rate, ST elevation, Sokolov index, number of premature ventricular complex, number of premature atrial complexes, ratio of non-conducted P waves, ratio of paced waves etc . . . .

"Neural network" refers to a mathematical structure taking an object as input and producing another object as output though a set of linear and non-linear operations called layers. Such structures have parameters which can be tuned through a learning phase so as to produce a particular output, and are for instance used for classification purposes. The input is then the object to categorize, and the output the probabilities to pertain in each of the categories.

"Convolutional neural network" refers to a neural network which is partly composed of convolutional layers, i.e. layers which apply a convolution on their input.

"Fully convolutional neural network" refers to a convolutional neural network in which all linear operations are convolutions.

"Recurrent convolutional neural network" refers to a particular convolutional neural network structure able to keep a memory on the previous objects it has been applied to.

"Lead invariant structure" refers to a structure proposed by the applicant to be able to use a same neural network for signals with any number of channels. Said structure is preferably used for neural networks processing Holters but not for networks processing standard 12 lead ECGs.

DETAILED DESCRIPTION

The present invention relates to temporal signal analysis, preferably cardiac signal analysis, using at least one convolutional neural network.

According to one embodiment, the cardiac signal is recorded from any number of leads during front 1 second to several days.

According to one embodiment, the cardiac signal is recorded from 12 leads or more. According to an alternative embodiment, the cardiac signal is recorded from strictly less than 12 leads.

According to one embodiment, the cardiac signal is recorded from 12 leads or more under direct medical supervision (resting ECG, stress test, etc.). According to an alternative embodiment, the cardiac signal is recorded from strictly less than 12 leads or not under direct medical supervision (ambulatory monitoring, etc.).

The framework used here is the one of supervised learning. The aim of supervised learning is to predict an output vector Y from an input vector X. In the Applicant embodiment, X is a cardiac signal (a multivariate signal) as a matrix of size m×n. As for Y, in the Applicant embodiment, it can be:
- the delineation, providing a score for each sample of X to be part of one of the different waves as a matrix of size p×n;
- the scores for each label as a vector of size q;
- the set composed of both the delineation and the vector of scores.

The problem of supervised learning can also be stated as follows: designing a function f such that for any input X, $f(X) \approx Y$. To this end, the function f is parametrized, and these parameters are "learned" (parameters are optimized with regards to an objective loss function, for example, by means of a gradient descent (Bishop, Pattern Recognition and Machine Learning, Springer, 2006, ISBN-10: 0-387-31073-8).

A neural network is a particular type of function f, aiming at mimicking the way biological neurons work. One of the most basic and earliest neural network is the perceptron (Rosenblatt, Psychological Review, Vol. 65, No. 6, 1958, pp 386-408). From the input X, it computes linear combinations (i.e. weighted sums) of the elements of X through a multiplication with a matrix W, adds an offset b, and then applies a non-linear function σ, such as for instance a sigmoid, on every element of the output:

$$f(X) = \sigma(WX+B)$$

The parameters which are learned in a perceptron are both W and B. In practice, more general neural networks are just compositions of perceptrons:

$$f(X) = \sigma_n(W_n \ldots \sigma_n(W_1 X + B_1) + B_n)$$

The output of a perceptron can be sent as input to another one. The input, the final output, and the intermediate states are called layers. The intermediate ones are more specifically called hidden layers, since only the input and the final output are observed. For instance, a neural network with one hidden layer can be written as:

$$f(X) = \sigma_2(W_2 \sigma_1(W_1 X + B_1) + B_2)$$

Such a network is shown in a graphic form as an example in FIG. 3. The vector X enters the network as the input layer, each element of the hidden layer is then computed from linear combinations of all elements of X (hence all the links), and the element of the output layer are then computed from linear combinations of all elements of the hidden layer.

It has been shown that neural networks in their general form are able to approximate all kinds of functions (Cvbenko, Math. Control Signals Systems, Vol. 2, 1989, pp 303-314). The term "deep learning" is used when a neural network is composed of many layers (though the threshold is not perfectly defined, it can be set to about ten). This field arose mostly in the last decade, thanks to recent advances in algorithms and in computation power.

Convolutional neural networks are a particular type of neural networks, where one or more of the matrices $W_1$ which are learned do not encode a full linear combination of the input elements, but the same local linear combination at all the elements of a structured signal such as for example an image or, in this specific context, a cardiac signal, through a convolution (Fukushima, Biol. Cybernetics, Vol. 36, 1980, pp 193-202, LeCun et al., Neural Computation, Vol. 1, 1989, pp 541-551). An illustration of a convolutional neural network is shown in FIG. 6. Most convolutional neural networks implement a few convolutional layers and then standard layers so as to provide a classification. A network which only contains convolutional networks is called a fully convolutional neural network. Finally, a recurrent convolutional neural network is a network composed of two sub-networks: a convolutional neural network which extracts features and is computed at all time points of the cardiac signal, and a neural network on top of it which accumulates through time the outputs of the convolutional neural network in order to provide a refined output. An illustration of a recurrent convolutional neural network is provided in FIG. 7.

As mentioned above, a cardiac signal, especially an ECG is represented as a matrix of real numbers, of size m×n. The constant m is the number of leads, typically 12, though networks can be taught to process cardiac signal with any number of leads, as detailed herebelow. The number of samples n provides the duration of the cardiac signal n f, with f being the sampling frequency of the cardiac signal. A network is trained for a given frequency, such as for example 250 Hz or 500 Hz or 1000 Hz, though any frequency could be used. A same network can however process cardiac signal of any length n, if it is fully convolutional or a recurrent neural network.

In both the delineation and the multi-label classification embodiments, networks are expressed using open softwares such as for example Tensorflow. Theano, Caffe or Torch. These tools provide functions for computing the output(s) of the networks and for updating their parameters through gradient descent. The exact structure of the network is not extremely important. Preferred choices are fUlly convolutional networks in the situation of the delineation network (Long et al., Proceedings of Computer Vision and Pattern Recognition, 2015, pp 3431-3440), convolutional (Ktizhevsk et al., Proceedings of Neural Information. Processing Systems, 2012, pp 1097-1105) in the situation of the multi-label classification network, or recurrent neural networks (Donahue et al., arXiv:1411.4389v3, 17 Feb. 2015 and Mnih et al., arXiv:1.406.6247v1, 24 Jun. 2014) for both the multi-label classification network and the delineation network. The 2D convolutional layers which were used on images are then easily converted into 1D convolutional layers in order to process cardiac signals.

In one embodiment, the network is amended to process data with varying number of leads in entry. In one embodiment, the neural network further comprises a sequence of layers at the beginning of the network so as to obtain a network which is independent of the number of input leads and can therefore process cardiac signals with any number of leads m. Such a structure is presented in FIG. 8 with m=2 input leads and k=3 output signals. The same structure can process any number of input leads m and will still provide k=3 signals in output, which can be fed to the rest of the network for which a fixed number of input signals is required. In this way, m need not be fixed anymore. According to one embodiment, in order to obtain a k-lead signal from an m-lead cardiac signal, the m leads are convoluted using a lead-by-lead convolution with k filters, the signal are then grouped by convolution filter in order to obtain k groups of in leads and a mathematical function is finally apply to each group to obtain k leads. According to one embodiment, any number of outputs k can be chosen. According to one embodiment, any number of inputs in can be used. According to one embodiment, the mathematical function is the maximum at each time point or may be any other function known to one skilled in the art. According to the Applicant, this feature was never disclosed before.

This invention also pertains to a method for manufacturing a neural network for delineation of a cardiac signal, by training it.

The training phase of the neural networks in the embodiment of delineation consists in the following steps:

taking one cardiac signal from a dataset containing cardiac signals and their known delineation; the cardiac signal being expressed as a matrix of size m×n with m fixed and at a predefined frequency;

expressing the delineation of this cardiac signal under the form of a matrix y of size p×n where p is the number of annotated types of wave; typically p=3, so as to identify P waves, QRS complexes, and T waves; annotations are expressed (P, 1.2s, 1.3s), (QRS 1.4s 1.7s), (T, 1.7, 2.1), (P, 2.2, 2.3); in this example, the first row of y, corresponding to P waves, will be 1 for samples corresponding to times between 1.2 and 1.3s, and between 2.2 and 2.4s, and 0 otherwise; row 2 will correspond to QRS complexes and row 3 to T waves;

computing the output of the network for this cardiac signal;

modifying the parameters of the network so as to decrease a cost function comparing the known delineation and the output of the network; a cross-entropy error function is used so as to allow for multi-labeling (allowing for multiple waves at a given instant); this minimization can be done though a gradient step repeating steps 1 to 4 at least once for each cardiac signal of the dataset;

recovering the neural network.

According to one embodiment, delineation further comprises wave characterization. According to said embodiment, p is the number of annotated types of wave plus the number of wave characterizations; for instance p=3+6=9 for identifying P waves, QRS complexes, and T waves, and characterizing premature waves, paced waves, ventricular QRS complexes, junctional QRS complexes, ectopic P waves and non-conducted P waves. According to said embodiment, annotations are expressed as lists of wave with their start and end points and characteristics such as for example: (P, 1.2s, 1.3s, [non-conducted]), (QRS 1.4s 1.7s, [premature, ventricular]), (1, 1.7, 2.1), (P, 2.2, 2.3); in this example, the first row of y, corresponding to P waves, wilt be 1 for samples corresponding to times between 1.2 and 1.3s, and between 2.2 and 2.4s, and 0 otherwise; row 2 will correspond to QRS complexes, row 3 to T waves, and row 4 corresponding to the premature characterization will be 1 during the premature QRS complex and 0 otherwise.

This invention also provides a method for manufacturing a neural network for the categorization of a cardiac signal, by training it.

In a multi-label classification, the manufacturing/training process includes the following steps:

taking one cardiac signal from a dataset containing cardiac signals and their known labels; the cardiac signal must be expressed as a matrix of size m×n with m fixed and at a predefined frequency;

expressing the labels as a vector of size q, with q the number of labels to identify; this vector could be [0; 1; 0; 0; 1; 0; 0; 0] for q=8; a 1 is set in the vector at the index corresponding to the labels which are present (i.e. having a score above at least one predefined threshold such has for instance 0.5): in the above example, the cardiac signal exhibits two labels;

computing the output of the network for this cardiac signal;

modifying the parameters of the network so as to decrease a cost function comparing the known label vector and the output of the network; a cross-entropy error function is used so as to allow for multi-labeling (allowing for multiple labels for a cardiac signal); this minimization can be done though a gradient step;

repeating steps 1 to 4 at least once for each cardiac signal of the dataset;

recovering the neural network.

This invention also provides a method for manufacturing a neural network for both the delineation and the categorization of a cardiac signal, by training it.

In the embodiment of the combination of delineation with multi-label classification, the manufacturing process includes the following steps:

taking one cardiac signal from a dataset containing cardiac signals and their known labels; the cardiac signal must be expressed as a matrix of size m×n with in fixed and at a predefined frequency;

expressing the labels as a vector of size q, with q the number of labels to identify; this vector could be [0; 1; 0; 0; 1; 0; 0; 0] for q=8; a 1 is set in the vector at the index corresponding to the labels which are present (i.e. above a predefined threshold): in the above example, the cardiac signal exhibits two labels;

expressing the delineation of this cardiac signal under the form of a matrix Y of size p×n where p is the number of waves to identify; typically p=3, so as to identify P waves, QRS waves, and T waves; annotations are usually expressed as lists wave type with their start and end points such as for example: (P, 1.2s, 1.3s), (QRS 1.4s 1.7s), (T, 1.7, 2.1), (P, 2.2, 2.3); in this example, the first row of Y, corresponding to P waves, will be 1 for samples corresponding to times between 1_2 and 1.3s, and between 2.2 and 2.4s, and 0 otherwise; row 2 will correspond to QRS complexes and row 3 to T waves;

computing both outputs of the network for this cardiac signal;

modifying the parameters of the network so as to decrease the sum of a cost function comparing the known label vector and one of the output of the network, and a cost function comparing the delineation and the other output; cross-entropy error functions are used to allow for multi-labeling (allowing for multiple labels for a cardiac signal as well as multiple waves at any time point); this minimization can be done though a gradient step;

repeating steps 1 to 4 at least once for each cardiac signal of the dataset;

recovering the neural network.

According to one embodiment, the step of expressing the delineation of the cardiac signal under the form of a matrix Y of size p×n further comprises wave characterization. According to said embodiment, p is the number of annotated types of wave plus the number of wave characterizations; for instance p=3+6=9 for identifying P waves, QRS complexes, and T waves, and characterizing premature waves, paced waves, ventricular QRS complexes, junctional QRS complexes, ectopic P waves and non-conducted P waves. According to said embodiment, annotations are expressed as lists of wave with their start and end points and characteristics such as for example: (P, 1.2s, 1.3s, [non-conducted]), (QRS 1.4s 1.7s, [premature, ventricular]), (T, 1.7, 2.1), (P, 2.2, 2.3); in this example, the first row of y, corresponding to P waves, will be 1 for samples corresponding to times between 1.2 and 1.3s, and between 2.2 and 2.4s, and 0 otherwise; row 2 will correspond to QRS complexes, row 3 to T waves, and row 4 corresponding to the premature characterization will be 1 during the premature QRS complex and 0 otherwise.

This invention also pertains to a method and a device for delineation of a cardiac signal, implementing a convolutional neural network, preferably a fully convolutional neural network, trained for delineation of a cardiac signal as described above.

As a basis, it shall be understood that the cardiac signal is expressed as a matrix X of size m×n at the frequency used for training the networks. The cardiac signal is used as input of the trained neural network.

The neural network then reads each time point of the cardiac signal, analyzes spatio-temporally each time point of the cardiac signal, assigns a temporal interval score to anyone of at least the following: P-wave, QRS complex, T-wave. It then recovers the output of the neural network, as a matrix Y of size p×n. An example is shown in FIG. 4: the first signal shows one of the leads of the ECG (to help the visualization), the following 3 signals are the outputs of the network, providing scores for P waves, QRS waves and T waves. As it can be seen, these scores are synchronized with the appearance of the aforementioned waves in the signal. According to one embodiment, when multiple leads cardiac signal is used, all the leads are processed simultaneously.

In a preferred embodiment, the neural network provides scores at each time point as a matrix Y, and a post-processing allows the allocation of each time point to none, single, or several waves, and provides the onset and offset of each of the identified waves as well as optionally its characterization. For instance, a sample can be affected to the waves for which the score on the corresponding row of Y is larger than 0.5. Wave characterization such as conductivity, prematurity and origin of the wave can be recovered from the activation of the corresponding row between the onset and the offset of the wave. The premature label can for instance be applied to the wave if the average of the row corresponding to the premature characterization is above 0.5 during the wave. This provides a delineation sequence of type (P, 1.2s, 1.3s, [non-conducted]), (QRS 1.4s 1.7s, [premature, ventricular]), (T, 1.7s, 2.1s), (P, 2.2s, 2.3s), as recorded in the annotations.

The invention also comprises a computer device implemented software comprising a trained neural network for delineation of a cardiac signal. The invention also comprises a device, such as for example a cloud server, a commercial ECG device, a mobile phone or a tablet, comprising a software implementing the method for delineation as described above.

According to one embodiment, the device further comprises a display configured for displaying the wave locations and optionally simultaneously the cardiac signal.

According to one embodiment, global measurements derived from the delineation sequence such as for instance the PR interval are displayed. According to one embodiment, global measurements derived from the delineation sequence are highlighted for values which are not in a normal range. According to one embodiment, local measurements such as for instance all. RR intervals are displayed with the cardiac signal. According to one embodiment, the conduction pattern of the cardiac signal is displayed in order to easily visualize characterization such as for instance prematurity of the waves with the cardiac signal. In an embodiment, the waves are displayed according to time with the cardiac signal.

This invention also pertains to a method and a device for multi-label classification of a cardiac signal, implementing Long-term Recurrent Convolutional Networks (LRCN, (Donahue et al., arXiv:1411.4389v3, 17 Feb. 2015). These neural networks are trained for multi-label classification of a cardiac signal as described above.

As a basis, it shall be understood that the cardiac signal is expressed as a matrix of size m×n at the frequency used for training the networks. Then, the cardiac signal is used as input of the trained neural network.

The neural network then reads each time point of the cardiac signal, analyzes temporally each time point of the cardiac signal, computes a score for each label, recovers the output of the neural network. In an embodiment, the labels are non-exclusive.

In an embodiment, some other information can be included as inputs of the network. Said information can be delineation-derived such as for instance PR interval duration, heart rate, ST elevation or amplitudes of the QRS waves. It can also be patient-based such as their age or any relevant clinical information.

In an embodiment, the neural network NN2 reads and analyzes each time point of the cardiac signal and further the global measurements obtained from NN1.

In a preferred embodiment, the neural network recovers the output as a vector of size q. This vector contains scores for the presence of each label. According to one embodiment, a label is considered as present if its score is above a predefined threshold. This threshold is usually set to 0.5. It can however be modified to provide a different sensitivity-specificity couple. Indeed, increasing the threshold leads to lower specificity and higher specificity, and conversely when decreasing it. This set of couples is called a receiver operating characteristics curve and any point of this curve can be chosen through a modification of the threshold.

The invention also comprises a computer device implemented software comprising a trained neural network for multi-label classification of a cardiac signal. The invention also comprises a device, such as for example a cloud server, a commercial ECG device, a mobile phone or a tablet, comprising a software implementing the method of multi-label classification of a cardiac signal as described above.

According to one embodiment, the device further comprises a display configured for displaying the scores of the labels which have been allotted to a time window and optionally simultaneously the cardiac signal.

According to an embodiment, the list of found labels for which the score in the vector are higher than a predefined threshold, typically 0.5 is displayed. Labels can also be added depending on the delineation (delineation-based label), such as for instance the label corresponding to first degree atrioventricular block which is equivalent to a PR interval longer than 200 ms, said PR interval being a global measurement based on the delineation. The list of labels can finally be filtered to remove redundant labels based on a known hierarchy of labels (for instance only the most detailed labels are retained), or aggregated through time on long cardiac signal so as to recover the start and end times of each abnormality.

This invention also pertains to a method and a device for delineation and multi-label classification of a cardiac signal, implementing a neural network trained for delineation and multi-label classification of a cardiac signal as described above.

As a basis, it shall be understood that the cardiac signal is expressed as a matrix of size m×n at the frequency used for training the networks. Then, the cardiac signal is used as input of the trained neural network.

The neural network then reads each time point of the cardiac signal, analyzes temporally each time point, assigns a temporal score to all of the following at least: P-wave, QRS complex, T-wave. It then computes a score for each labels, recovers both the outputs of the neural network: the first as a matrix y of size p×n, providing scores for at least P waves, QRS waves and T waves; and the second as a vector of size q, said vector containing scores for the presence of each label.

In a preferred embodiment, a post-processing of the delineation output allows to affect each time point to none, single, or several waves, and provides the onset and offset of each of the identified waves. For instance, a sample can be affected to the waves for which the score on the corresponding row of Y is larger than 0.5. This provides a delineation sequence of type (P, 1.2s, 1.3s), (QRS 1.4s 1.7s), (T, 1.7s, 2.1s), (P, 2.2s, 2.3s), as recorded in the annotations.

According to an embodiment, the list of found labels for which the score in the vector are higher than a predefined threshold, typically 0.5, are displayed; as well as the delineation, optionally with the cardiac signal.

According to an embodiment of the invention, a step to prepare the signal and create input variables for classification is further carried out ("pre-treatment"). The purpose of this pre-treatment is to remove the disturbing elements of the signal such as for example noise and baseline, low frequency signal due to respiration and patient motion, in order to facilitate classification. For noise filtering, a multivariate approach functional analysis proposed by (Pigoli and Sangalli, Computational Statistics and Data Analysis, vol.56, 2012, pp 1482-1498) can be used. The low frequencies of the signal corresponding to the patient's movements may be, removed using median filtering as proposed by (Kaur et al., Proceedings published by International Journal of Computer Applications, 2011, pp 30-36).

According to an embodiment of the invention, a post-treatment step is added, so as to produce the onset and offset of each wave in the cardiac signal.

The invention also comprises a computer device implemented software comprising a trained neural network for delineation and multi-label classification of a cardiac signal. The invention also comprises a device, such as for example a cloud server, a commercial ECG device, a mobile phone or a tablet, comprising a software implementing the method of delineation and multi-label classification of a cardiac signal as described above.

According to one embodiment, the device further comprises a display configured for displaying the wave locations, the scores of the labels which have been allotted to a time window and optionally simultaneously the cardiac signal.

In an embodiment, global and local measurements derived from the delineation sequence such as for instance the PR interval are displayed. In an embodiment, the global and local measurements derived from the delineation sequence are highlighted for values which are not in a normal range. In an embodiment, the conduction pattern of the cardiac signal is displayed in order to easily visualize characterization such as for instance prematurity of the waves; and the waves may be displayed according to time.

The present invention further relates to a system comprising an electrocardiograph for recording cardiac signal and for implementing the methods according to the present invention. Thus, the electrocardiograph provides labels, delineation, measurements and conduction pattern of the cardiac signal right after the recording.

This invention brings to the art a number of advantages, some of them being described below:

- The input of the networks are one or multi-lead cardiac signals with variable length, possibly preprocessed so as to remove noise and baseline wandering due to patients movements, and express the signal at a chosen frequency.
- Using the presented lead invariant structure, a same network can handle cardiac signals with different number of leads.
- The output of a classification network is a vector of scores for labels. These are not classification scores since one cardiac signal can present several labels. For example, the output of such network could be a vector [0.98; 0.89; 0.00; . . . ] with the corresponding labels for each element of the vector (Right Bundle Branch Bloc; Atrial Fibrillation; Normal ECG; . . . ). Scores are given between a scale of [0, 1] and the above example output vectors therefore indicates a right bundle branch block and atrial fibrillations. A recurrent neural network architecture can be added on the top of the convolutional network (Donahue et al., arXiv:1411.4389v3, 17 Feb. 2015 and Mnih et al., arXiv:1406.6247v1, 24 Jun. 2014). In this way, the convolution network acts as a pattern detector whose output will be accumulated in time by the recurrent network.
- The output of the delineation network is a set of signals spanning the length of the input cardiac signal, providing the score for being in waves such as for instance P waves, QRS complexes, a T waves and potentially other types of waves or segments such as for example flutter waves, U waves or noisy segments. An example of output signals is provided in FIG. 5.
- The delineation network can also characterize the waves such as for instance their prematurity, conductivity and ectopy. This ability allows to unify two steps of the delineation which are separate in current methods, making the proposed method more reliable and able to leverage context information for the waves characterization.
- The delineation network is not limited to recovering at most one wave at each time point and therefore can identify several waves at any time point, such as for instance P waves hidden in a T wave.
- The delineation network allows both the recovery of the start and end of each wave and there characterization in a single step, which is more reliable than all previous methods. In particular in is more reliable to recover P waves and characterize them, allowing to provide the conductivity pattern of the cardiac signal.
- No works applying convolutional networks to the delineation have been made so far.
- The underlying structure of the networks is not fundamental as long as they are convolutional neural networks. One can use a structure such as RLCN (Donahue et at, arXiv:1411.4389v3, 17 Feb. 2015 and Mnih et al., arXiv:

1406.6247v1, 24 Jun. 2014) for classification and a network similar as the one in (Long et al., Proceedings of Computer Vision and Pattern Recognition, 2015, pp 3431-3440) for delineation. In both embodiments, convolutional layers must be modified as 1D convolutions instead of 2D convolutions. On top of these architectures, both embodiments can use a lead invariant structure such as but not limited to the one presented in FIG. 8.

A hybrid network, sharing the first layers and diverging so as to provide both the delineation as one output, and the multi-label classification as another output is also used. This combination has the advantage of being able to produce a multi-label classification helped by the identification of the cardiac signal waves.

EXAMPLES

The neural networks used within the present invention, were filed at LOGITAS under number D16201.

The present invention is further illustrated by the following examples.

Example 1

Training for Delineation

This training was performed on 2204 ECGs and the network evaluated on about 900 beats from 77 different patients which were not used for the training phase. The following table provides the precision of the wave onsets (beginnings) and offsets (ends) in term of bias and standard deviation (std) as well as the false positive (FP) and false negative (FN) rates of the waves detection and of their characterizations:

|  | FP (%) | FN (%) | Bias (ms) | Std (ms) | Count |
|---|---|---|---|---|---|
| P | 7.9 | 5.6 | 0.9 | 10.6 | 730 |
| PQ | 0 | 0.3 | 0.3 | 7.2 | 616 |
| QRS | 0 | 0 | 1.8 | 5.2 | 887 |
| QT | 0 | 0.1 | 0.7 | 13.3 | 873 |
| P onset | N/A | N/A | −2.9 | 6.4 | 689 |
| P offset | N/A | N/A | −2 | 8.4 | 689 |
| QRS onset | N/A | N/A | −3.1 | 4 | 887 |
| QRS offset | N/A | N/A | −1.3 | 3.6 | 887 |
| QT offset | N/A | N/A | −2.3 | 12.3 | 872 |
| ectopic P | 6 | 16 | N/A | N/A | 75 |
| premature P | 0 | 20 | N/A | N/A | 10 |
| paced P | 0 | 24.3 | N/A | N/A | 37 |
| non-conducted P | 0 | 8.3 | N/A | N/A | 36 |
| ventricular QRS | 2.7 | 5.3 | N/A | N/A | 38 |
| premature QRS | 8.3 | 15.4 | N/A | N/A | 26 |
| paced QRS | 0 | 0 | N/A | N/A | 22 |
| junctional QRS | 0 | 14.6 | N/A | N/A | 48 |

Concerning hidden P waves, the proposed algorithm was able to recover 75 out of 87 hidden P waves present in this evaluation dataset, while other algorithms would not be able to find any of them.

From the onsets and offsets of each wave are derived standard global measurements such as the P duration, PR interval, QRS duration and QT interval. An evaluation was performed on the standard CSE dataset which provides acceptance limits for delineation algorithms (Christov et al. BioMedical Engineering OnLine, 2006, vol. 5, pp. 31-38), yielding the following results which are well within the acceptance range:

|  | Standard Deviation (ms) | | Bias (ms) | |
|---|---|---|---|---|
| Measurement | Result | Limit | Result | Limit |
| P | 3.8 | 15 | −2.4 | 10 |
| PQ | 6.1 | 10 | 0.1 | 10 |
| QRS | 4.2 | 10 | 2.0 | 10 |
| QT | 7.2 | 30 | −14.2 | 25 |

The following table sums up the results on the MIT-BIH Arrhythmia Database (Moody et al, Computers in Cardiology, 1990, vol. 17, pp.185-188) of a delineation network with a lead-invariant structure, which was not used for the training, in terms of QRS and premature ventricular complexes (PVC) detections:

|  | FP (%) | FN (%) | Count |
|---|---|---|---|
| QRS | 0.32 | 0.17 | 107341 |
| PVC | 7.68 | 15.10 | 7071 |

Compared with state-of-the-art algorithms, the precision was improved and the ability of the algorithm, which can find the waves and characterize them at the same time, is much more efficient. In FIG. 5 for instance, the ECG exhibits an atrioventricular block which means that the 1' waves and the QRS complexes are completely decoupled. In this example, the P waves are regular and QRS complexes happen at random times. One can observe in this example that the algorithm correctly found two P waves between the first ORS complex and the second QRS complex, while most algorithms would not be able to find them since they look for only one P wave before each complex. The last P wave also starts before the end of the last T wave, adding complexity. Finally, the algorithm is able to characterize theses waves as non-conducted. Other algorithms would not have been able to find the hidden waves and would not have been able to characterize any wave as non-conducted.

Example 2

Training for Multi-Label Classification

A network has been trained using about 85,000 ECGs and has been evaluated on a dataset representative of a hospital emergency unit including 1,000 patients which were not used in the training phase. The results in terms of accuracy, specificity, sensitivity, and positive predict values were the following for some of the searched labels:

|  | Population | Accuracy | Sensitivity | Specificity | PPV |
|---|---|---|---|---|---|
| Normal ECG | 421 | 77.39% | 66.75% | 89.06% | 87.00% |
| Atrial fibrillation | 22 | 99.75% | 90.91% | 100.00% | 100.00% |
| Atrial flutter | 3 | 99.88% | 66.67% | 100.00% | 100.00% |
| Junctional rhythm | 5 | 99.75% | 80.00% | 99.88% | 80.00% |
| Pacemaker | 5 | 100.00% | 100.00% | 100.00% | 100.00% |
| Premature ventricular complex(es) | 17 | 99.63% | 88.24% | 99.87% | 93.75% |
| Complete right bundle branch block | 21 | 99.50% | 90.48% | 99.74% | 90.48% |
| Complete left bundle branch block | 4 | 99.75% | 75.00% | 99.88% | 75.00% |

|  | Population | Accuracy | Sensitivity | Specificity | PPV |
|---|---|---|---|---|---|
| Left ventricular hypertrophy | 7 | 99.38% | 57.14% | 99.75% | 66.67% |
| Acute STEMI | 5 | 100.00% | 100.00% | 100.00% | 100.00% |
| Old MI | 27 | 93.79% | 70.37% | 94.60% | 31.15% |

A neural network with a lead-invariant structure aimed at classifying rhythm abnormalities was also trained. Its performance on Holter ECGs in term of atrial fibrillation was analyzed on the MIT-BIH Arrhythmia Database (Moody et al, *Computers in Cardiology*, 1990, vol. 17, pp.185-188) comprising 30 minutes 2-lead ECGs of 48 different patients. To this end, the neural networks analyzed all 20 second segments of the ECG, which providing a rhythm label each 20 second, which were aggregated to provide the beginning and end of each rhythm abnormality or descriptor. The recovered labels were compared to the reference annotations, yielding a, accuracy, sensitivity, specificity and positive predictive value (PPV) for the atrial fibrillation label and the less specific atrial fibrillation or flutter label:

|  | Accuracy | Sensitivity | Specificity | PPV |
|---|---|---|---|---|
| Atrial fibrillation | 98.3% | 96.9% | 98.5% | 89.6% |
| Atrial fibrillation or flutter | 99.0% | 96.8% | 99.2% | 92.3% |

These results are similar to the state-of-the-art in term of sensitivity, but significantly better than state-of-the-art methods in term of specificity and therefore also in accuracy and PPV.

A graphical representation of how a standard multi-label is used on ECGs is displayed in FIG. 6. The ECG is given as input to the network, which aggregates the information locally and then combines it layer by layer to produce a high-level multi-label classification of the ECG, in this example correctly recognizing atrial fibrillations and a right bundle branch block. Such networks however take a fixed size as input and the process must be reproduced at different locations so as to analyze the whole signal. FIG. 7 is an example of a graphic representation of a recurrent neural network which overcomes this issue. This type of network is made from a standard convolutional network computed at all possible locations of the signal, and on top of which comes another network layer which accumulates the information. In this example, the network correctly recognizes a premature ventricular complex (PVC, the fifth and largest beat) in the first part of the signal while the second part of the signal is considered as normal. The accumulated output is therefore PVC since this ECG has an abnormality and cannot therefore be considered as normal.

Example 3

Delineation and Multi-Label Classification

In another embodiment, the applicant combines features described above in examples 1 and 2. Such combination enables to combine the advantages of both networks in a unique network, providing similar results for both the delineations and the multi-label classifications.

Example 4

Platform Use Case

According to one embodiment, a user can log into a web platform. An upload button is available for the user to upload one of their ECGs in a supported formal so as to process it. The user is then redirected to a page displaying the ECG as shown in FIG. 9. The user can than select to show the detected abnormalities as shown in FIG. 10. In this case, the neural networks correctly detected a second degree atrioventricular block Mobitz 1 (a lengthening of the PR interval leading to a non-conducted P wave) and an intraventricular block (causing a lengthened QRS duration). The user can also choose to display the delineation information as shown in FIG. 11. This information includes highlighting of the identified waves on the ECG drawing, printing global measurements derived from the delineation above the ECG drawing such as for example heart rate (HR) and QRS duration (QRS), with highlighting of the values which are not in a normal range such as for instance a QRS duration larger than 110 ms. Local measurements such as all RR intervals are also shown as figures under the ECG. It also includes a laddergram-like feature showing the conduction pattern of the waves, their prematurity and their origin. This feature is displayed under the ECG, with each dot on the first line being a P wave, each dot of the second wave being a QRS wave and lines between them implying conduction. One can observe in this case that some P waves are not conducted. These same P waves are hidden P waves since they occur during T waves. In FIGS. 12 and 13, one can see different examples of the conduction pattern display where the prematurity of the P and QRS waves are shown (with surrounding squares), and the origin of the waves are also shown (lightning bolt for a paced wave, square for ectopic P wave or ventricular QRS complex, triangle for junctional QRS complex etc).

Example 5

Application Programming Interface (API) Use Case

According to an embodiment, a user can also send an ECG through an API. The ECG is received on the platform and analyzed. The user can then recover information such as the delineation and the multi-label classification through another API.

Example 6

Resting ECG Interpretation

A patient arrives at the emergency unit of a hospital and an ECG is performed. The ECG shows wide complex tachycardia. Such a pattern can occur in very different situations, such as in the case of ventricular tachycardia, or with both atrial fibrillation and Wolff-Parkinson-White syndrome, or with both a bundle branch block and sinus tachycardia. Such conditions must be treated differently, the two former being life-threatening. Standard algorithms of the prior art can only detect one abnormality at a time and not a combination of labels. In this case, it is however crucial to be able to perform multi-label classification since interpretations may imply a combinations of labels. Being able to do so help properly identifying an actual ventricular tachycardia that other algorithms have difficulty to identify such as the one in FIG. 14 indeed, method according to the present invention is able to test all other possible combinations of labels and rule them out. Also, during an examination a general practitioner performs an ECG on a patient. The delineation is then helpful in order to highlight hidden P waves which may completely change the diagnostic between normal sinus rhythm and a 2' degree atrioventricular block which may require the use of a pacemaker.

Example 7

Holter Interpretation

A patient is prescribed a 7 day Holter. The 7 days must afterwards be interpreted by a specialist. The proposed algorithm is able to identify noisy segments of the signal which are common in Holters since the patient is allowed to move. It can also find atrial fibrillation or atrial flutter which is often looked at in Hollers. Thanks to its multi-label ability, the proposed algorithm can also find atrial fibrillation during noise segments. In other situations, the patient could be monitored at a hospital in order to assess the possibility of an acute myocardial infarction. The proposed method can then provide ST elevations through time thanks to the delineation (amplitude at the QRS offset minus amplitude at the QRS onset) which changes are a very important indicator of STEMI (ST elevation myocardial infarction).

Figure 1:
FIG. 1 is a photo of an ECG.
Figure 2:
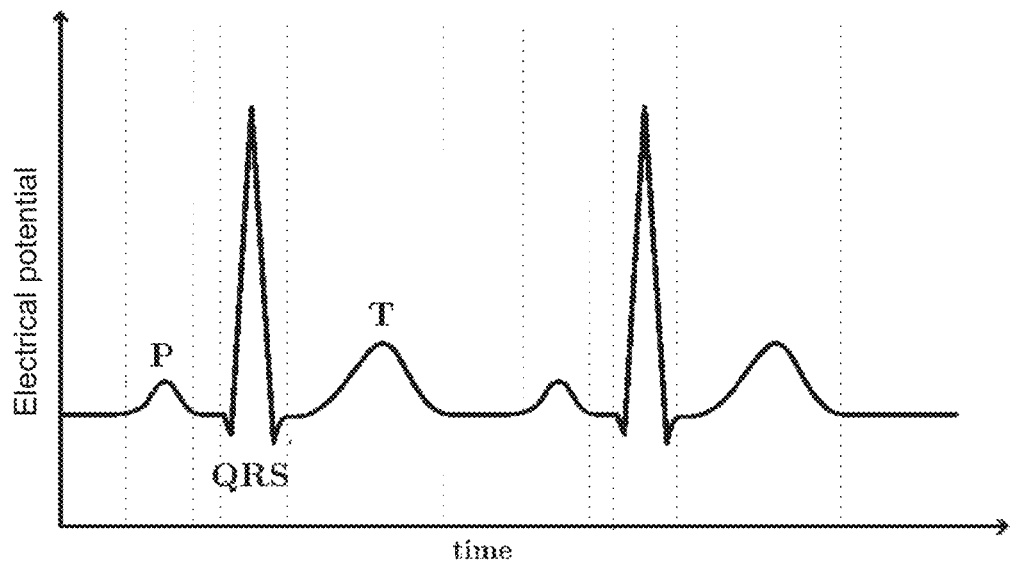
FIG. 2 is a schematic representation of a notinal ECG, with the P wave, the QRS complex/wave comprising the Q, R, S and J points, and the T wave.
Figure 3:
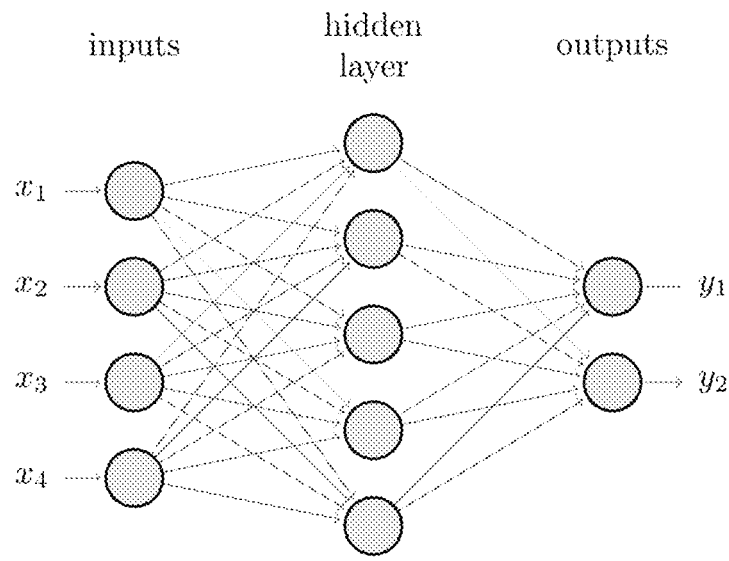
FIG. 3 is an example of structure for a basic neural network with no convolutional layer.
Figure 4:
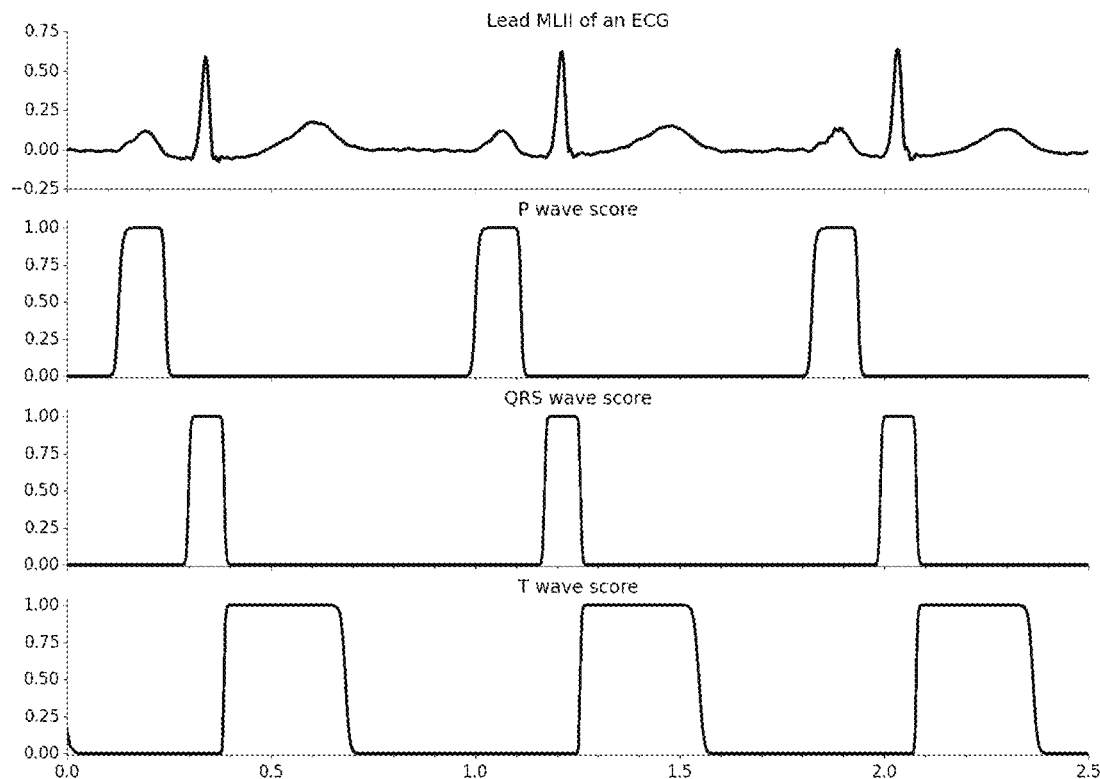
FIG. 4 is an example of the output of the delineation network on a normal ECG.
Figure 5:
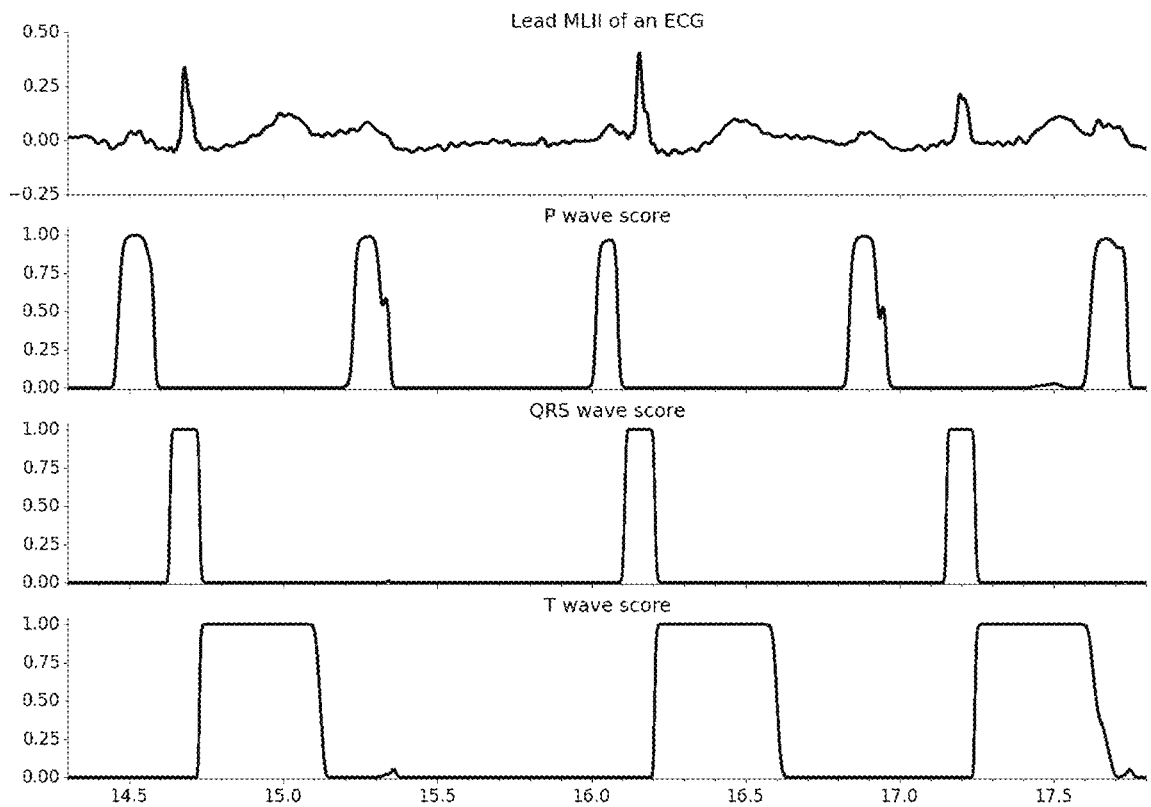
FIG. 5 is an example of the output of the delineation network on an ECG with hidden P waves (high degree atrioventricular block).
Figure 6:
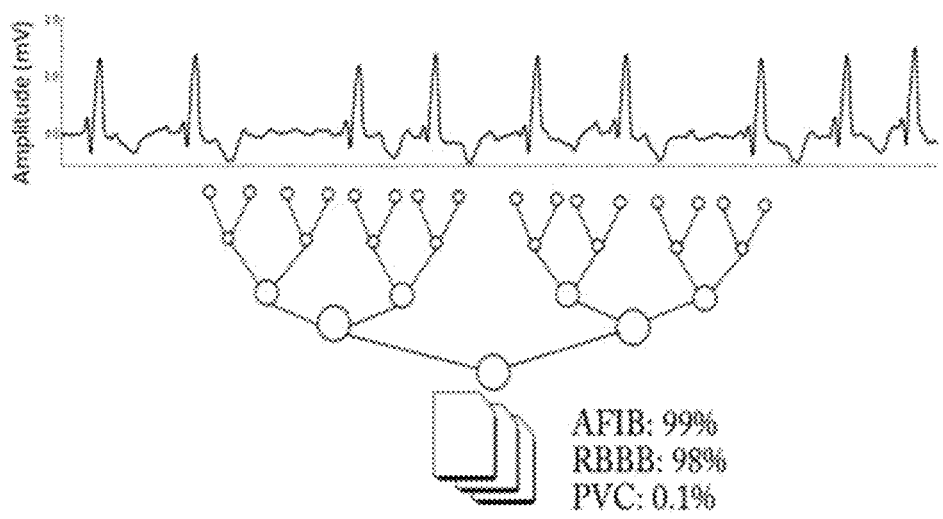
FIG. 6 models the way a standard multi-label convolutional network works.
Figure 7:
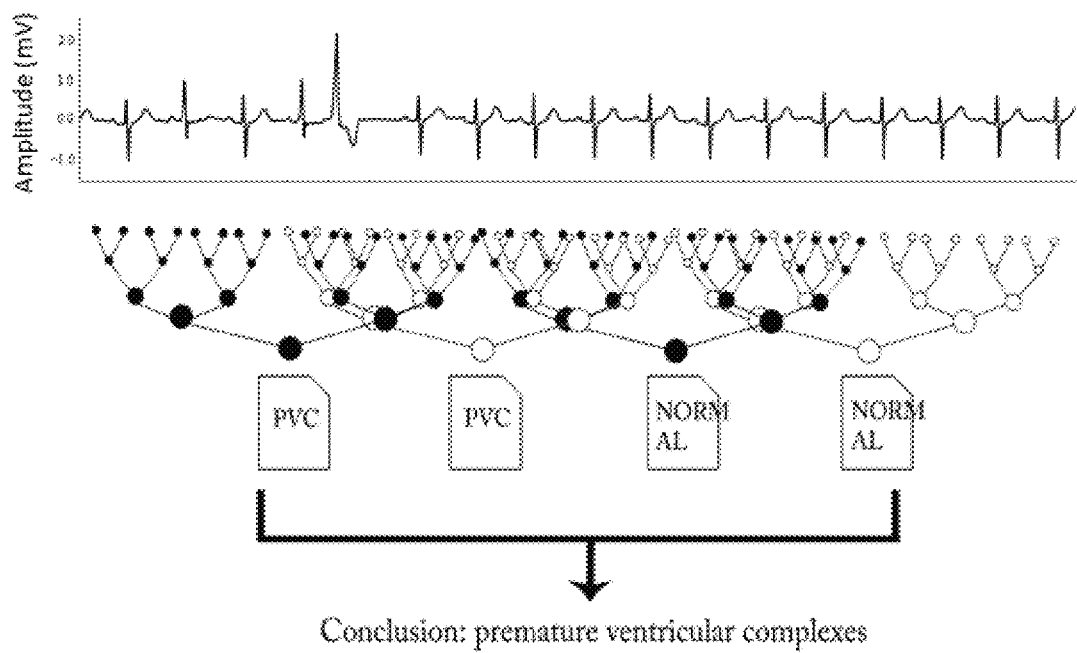
FIG. 7 models the way a multi-label recurrent convolutional network works.
Figure 8:
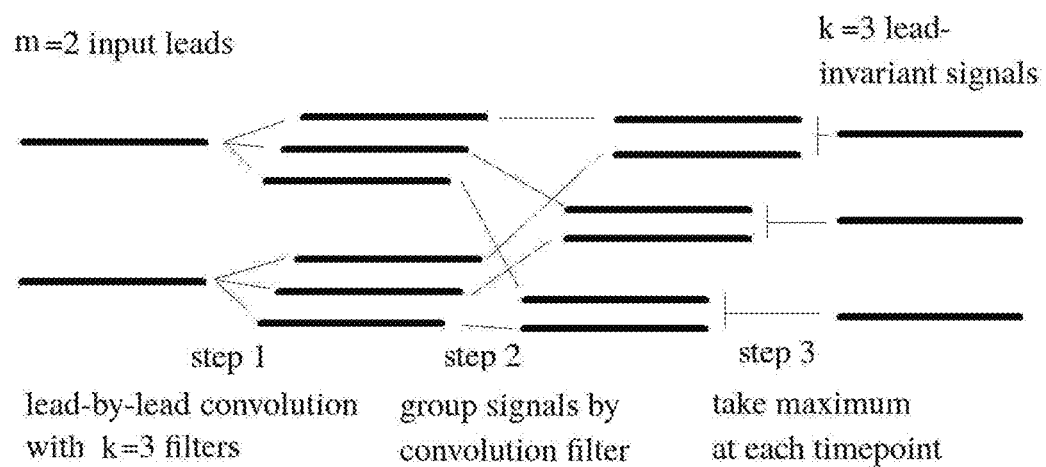
FIG. 8 provides an example of structure to use as first layers of a neural network to make it able to process any number of leads.
Figure 9:
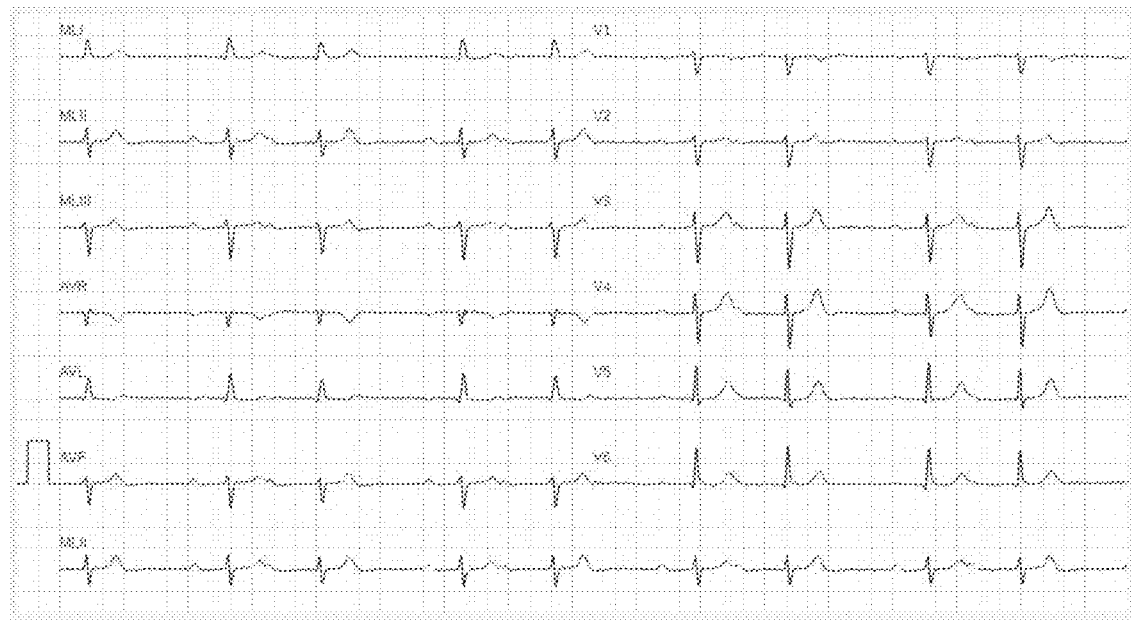
FIG. 9 shows the interface after loading an ECG.
Figure 10:
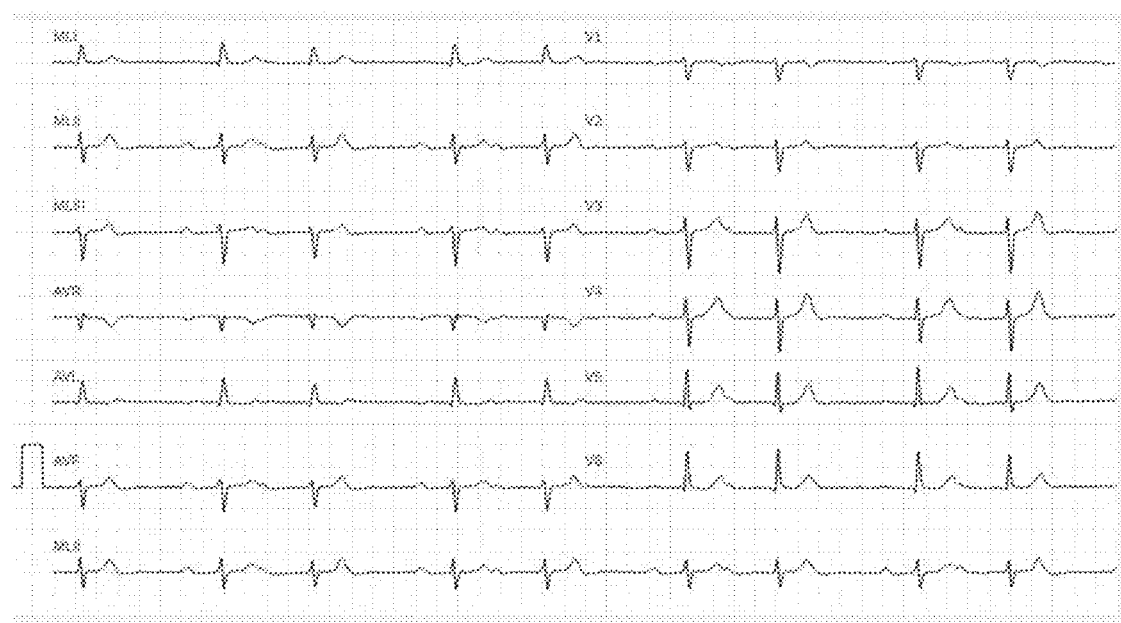
FIG. 10 shows the interface with the ECG and the labels provided by the multi-label classification algorithm.
Figure 11:
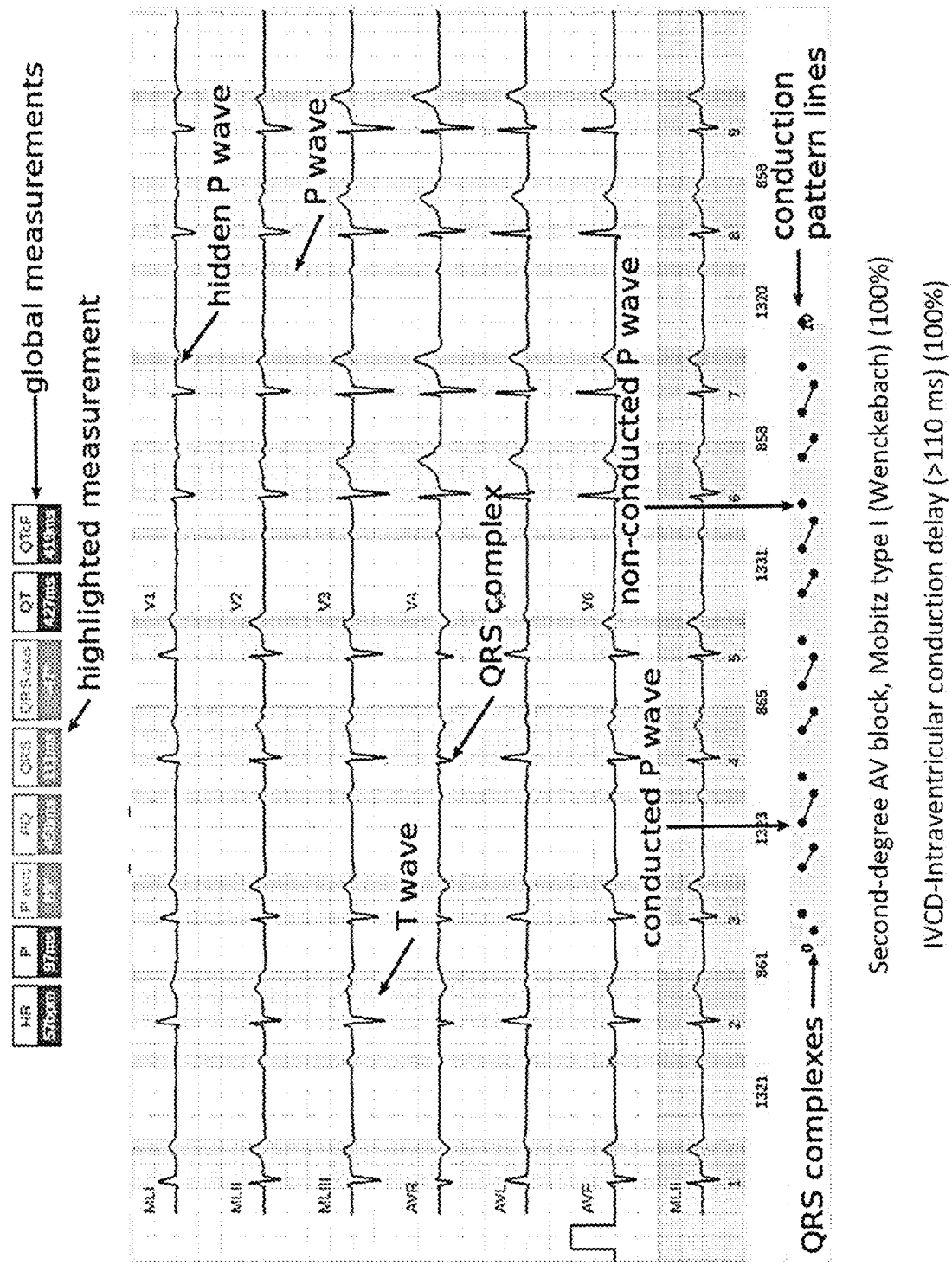
FIG. 11 shows the interface with the ECG, the labels provided by the multi-label classification algorithm, the delineation of the waves on the ECG, measurements derived from the delineation above the ECG with highlighted abnormal values, and conduction pattern under the ECG derived from the delineation. Some waves, including one hidden P wave are more specifically shown.
Figure 12:
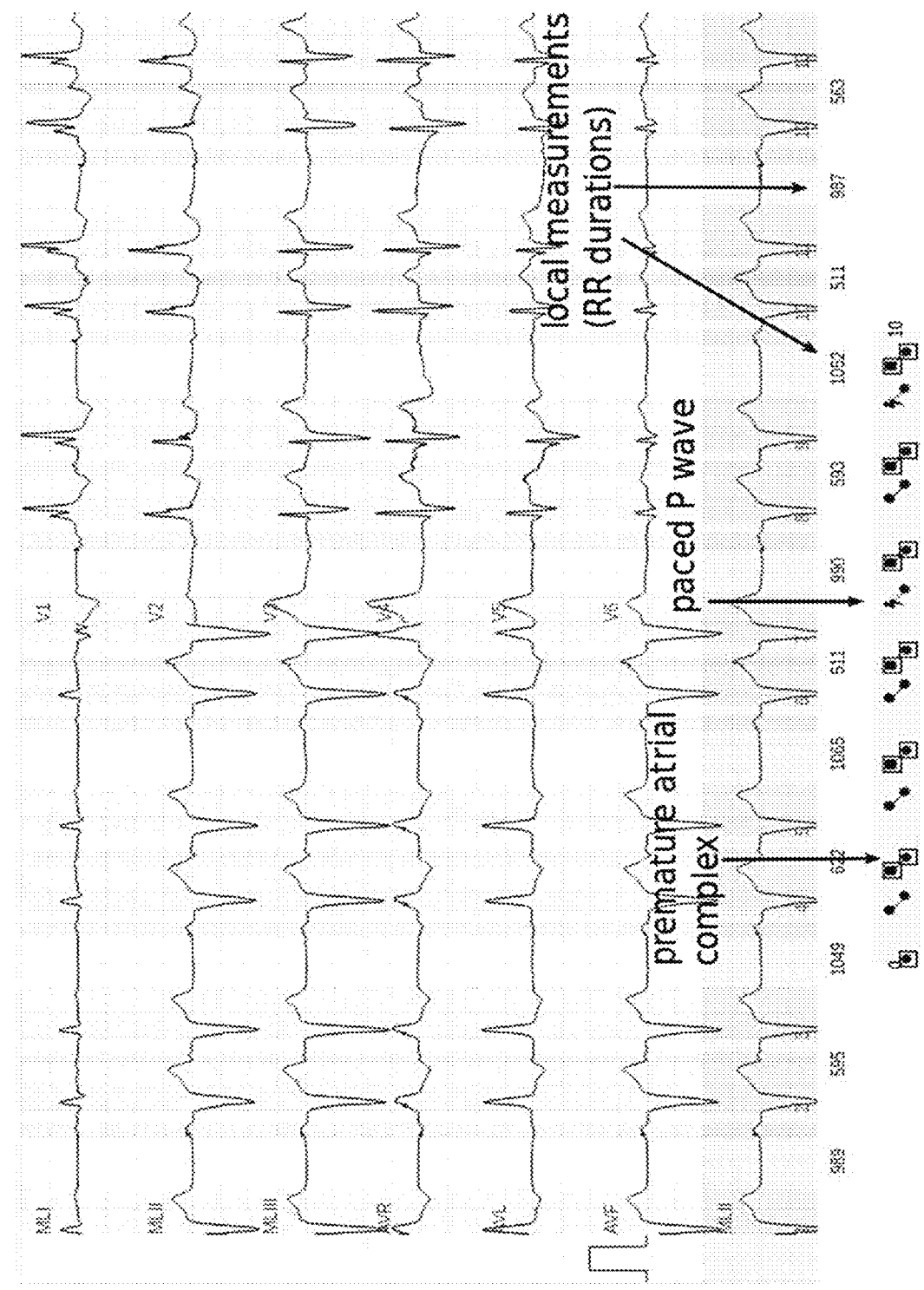
FIG. 12 shows an example ECG with its conduction pattern comprising premature atrial complexes and one paced P waves. This conduction pattern is composed of a first line with the P waves as dots, and a second line with the QRS as dots. It can be synchronized or not with the signal depending on its use (not synchronized on this example).
Figure 13:
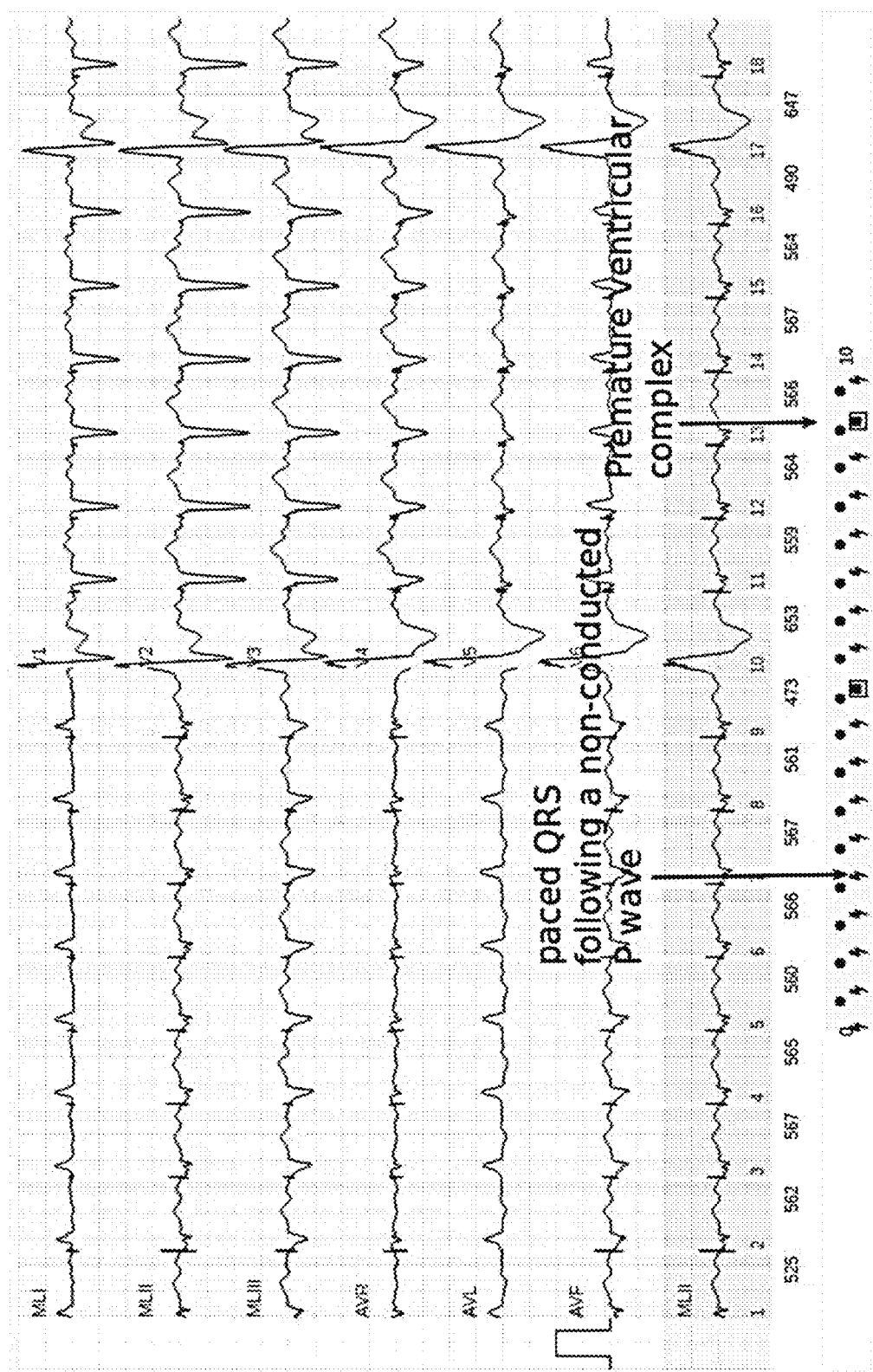
FIG. 13 shows an example ECG with its conduction pattern comprising non-conducted P waves, paced QRS complexes and premature ventricular complexes. These elements are pointed at on the figure.
Figure 14:
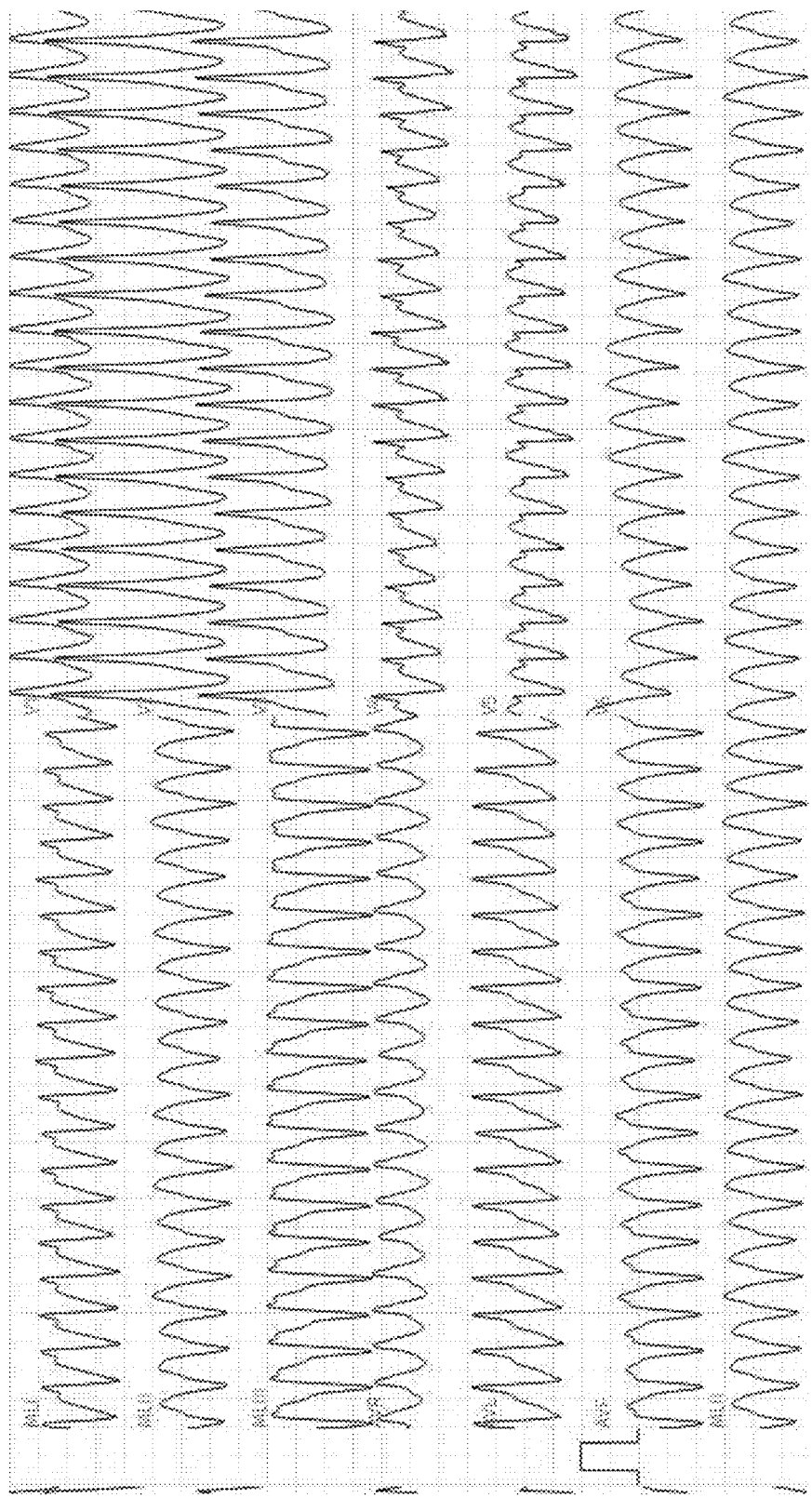
FIG. 14 shows an ECG with a ventricular tachycardia which was not identified by a prior art algorithm but is correctly identified by the proposed algorithm.

The invention claimed is:

1. A computerized method for detecting abnormalities in an electrocardiogram (ECG) signal obtained from a patient, the computerized method comprising:
   receiving the ECG signal sampled at a plurality of time points;
   generating at least one matrix representative of at least a portion of the ECG signal;
   computing delineation scores of the ECG signal at each time point of the plurality of time points of the at least a portion of the ECG signal, the delineation scores corresponding to multiple wave types associated with the ECG signal at each time point using the at least one matrix;
   computing anomaly scores to detect anomalies associated with the ECG signal using the at least one matrix and the delineation scores;
   determining that an anomaly is present based on the anomaly scores; and
   generating information to indicate the presence of the anomaly associated with the ECG signal based on determining that the anomaly is present.

2. The computerized method of claim 1, further comprising denoising and removing a baseline of the ECG signal.

3. The computerized method of claim 1, wherein determining that the anomaly is present comprises determining that atrial fibrillation is present.

4. The computerized method of claim 1, further comprising causing display of the information to indicate the presence of the anomaly.

5. The computerized method of claim 4, wherein causing the display further comprises causing display of a representation of the ECG signal along with the information to indicate the presence of the anomaly.

6. The computerized method of claim 1, wherein computing the anomaly scores comprises applying the at least one matrix to at least one trained neural network to compute the anomaly scores.

7. The computerized method of claim 6, further comprising training at least one neural network with a dataset of pre-characterized ECG signals to generate the at least one trained neural network.

8. The computerized method of claim 6, wherein the at least one trained neural network comprises a first neural network for classification.

9. The computerized method of claim 6, wherein the at least one trained neural network further comprises a second neural network for delineation.

10. The computerized method of claim 1, further comprising:
    determining that at least one additional anomaly is present based on the anomaly scores; and
    generating information to indicate the presence of the at least one additional anomaly associated with the ECG signal based on determining that the at least one additional anomaly is present.

11. The computerized method of claim 1, wherein generating the information to indicate the presence of the anomaly comprises assigning an anomaly label to the ECG signal for the anomaly.

12. The computerized method of claim 1, wherein determining that the anomaly is present based on the anomaly scores comprises comparing the anomaly scores to at least one threshold value.

13. The computerized method of claim 1, wherein generating the at least one matrix comprises generating the at least one matrix of size m×n where "m" is a number of leads of a cardiac sensor used to obtain the ECG signal and "n" is a number of time points of the plurality of time points.

14. The computerized method of claim 1, wherein generating the at least one matrix comprises generating the at least one matrix of size p×n where "p" is a number of cardiac wave types and "n" is a number of time points of the plurality of time points.

15. The computerized method of claim 1, further comprising expressing a plurality of detected anomalies as a vector of size q, with q being a number of anomalies to identify.

16. The computerized method of claim 1, further comprising determining whether at least one type of cardiac wave is present at each time point of the plurality of time points.

17. The computerized method of claim 1, further comprising determining that the at least a portion of the ECG signal is normal based on the anomaly scores.

18. A system for detecting abnormalities in an electrocardiogram (ECG) signal obtained from a patient, the system comprising at least one server and at least one processor configured to execute instructions to:
receive the ECG signal sampled at a plurality of time points;
generate at least one matrix representative of at least a portion of the ECG signal;
compute delineation scores of the ECG signal at each time point of the plurality of time points of the at least a portion of the ECG signal, the delineation scores corresponding to multiple wave types associated with the ECG signal at each time point using the at least one matrix;
compute anomaly scores to detect anomalies associated with the ECG signal using the at least one matrix and the delineation scores;
determine that an anomaly is present based on the anomaly scores; and
generate information to indicate the presence of the anomaly associated with the ECG signal based on the determination that the anomaly is present.

19. The system of claim 18, wherein to determine that the anomaly is present comprises determine that atrial fibrillation is present.

20. The system of claim 18, wherein the at least one processor is configured to execute instructions to cause display of the information to indicate the presence of the anomaly.

21. The system of claim 20, wherein the at least one processor is configured to execute instructions to cause display of a representation of the ECG signal along with the information to indicate the presence of the anomaly.

22. The system of claim 18, wherein to compute the anomaly scores comprises applying the at least one matrix to at least one trained neural network to compute the anomaly scores.

23. The system of claim 22, wherein the at least one processor is configured to execute instructions to train at least one neural network with a dataset of pre-characterized ECG signals to generate the at least one trained neural network.

24. The system of claim 22, wherein the at least one trained neural network comprises a first neural network for classification.

25. The system of claim 24, wherein the at least one trained neural network further comprises a second neural network for delineation.

26. The system of claim 18, wherein the at least one processor is configured to execute instructions to:
determine that at least one additional anomaly is present based on the anomaly scores; and
generate information to indicate the presence of the at least one additional anomaly associated with the ECG signal based on the determination that the at least one additional anomaly is present.

27. The system of claim 18, wherein the at least one processor is configured to execute instructions to determine whether at least one type of cardiac wave is present at each time point of the plurality of time points.

28. The system of claim 18, wherein the at least one processor is configured to execute instructions to determine that the at least a portion of the ECG signal is normal based on the anomaly scores.

29. A programmed routine for use with a computerized system for detecting abnormalities in an electrocardiogram (ECG) signal obtained from a patient, the programmed routine comprising instructions that when executed:
receive the ECG signal sampled at a plurality of time points;
generate at least one matrix representative of at least a portion of the ECG signal;
compute delineation scores of the ECG signal at each time point of the plurality of time points of the at least a portion of the ECG signal, the delineation scores corresponding to multiple wave types associated with the ECG signal at each time point using the at least one matrix;
compute anomaly scores to detect anomalies associated with the ECG signal using the at least one matrix and the delineation scores;
determine that an anomaly is present based on the anomaly scores; and
generate information to indicate the presence of the anomaly associated with the ECG signal based on the determination that the anomaly is present.

30. The programmed routine of claim 29, wherein to determine that the anomaly is present comprises determine that atrial fibrillation is present.

* * * * *